(12) United States Patent
Yoshii et al.

(10) Patent No.: US 12,256,942 B2
(45) Date of Patent: Mar. 25, 2025

(54) ENDOSCOPIC TREATMENT DEVICE

(71) Applicant: OLYMPUS MEDICAL SYSTEMS CORP., Hachioji (JP)

(72) Inventors: Toshihiro Yoshii, Hachioji (JP); Naoki Takizawa, Musashino (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 0 days.

(21) Appl. No.: 18/594,295

(22) Filed: Mar. 4, 2024

(65) Prior Publication Data

US 2024/0206883 A1 Jun. 27, 2024

Related U.S. Application Data

(63) Continuation of application No. 17/584,741, filed on Jan. 26, 2022, now Pat. No. 11,944,321.

(60) Provisional application No. 63/141,620, filed on Jan. 26, 2021.

(51) Int. Cl.
*A61B 17/128* (2006.01)
*A61B 17/122* (2006.01)
*A61B 17/00* (2006.01)

(52) U.S. Cl.
CPC ...... *A61B 17/1285* (2013.01); *A61B 17/1227* (2013.01); *A61B 2017/00477* (2013.01)

(58) Field of Classification Search
CPC .............. A61B 17/122; A61B 17/1227; A61B 17/1285; A61B 2017/00477
See application file for complete search history.

(56) References Cited

U.S. PATENT DOCUMENTS

| 3,958,576 | A | 5/1976 | Komiya |
| 4,367,746 | A | 1/1983 | Derechinsky |
| 5,242,456 | A | 9/1993 | Nash et al. |
| 5,569,274 | A | 10/1996 | Rapacki et al. |

(Continued)

FOREIGN PATENT DOCUMENTS

| EP | 1 547 529 A1 | 6/2005 |
| JP | 2002-191609 A | 7/2002 |

(Continued)

OTHER PUBLICATIONS

Oct. 8, 2024 Notice of Allowance issued in Japanese Patent Application No. 2023-504974.

(Continued)

*Primary Examiner* — Ryan J. Severson
(74) *Attorney, Agent, or Firm* — Oliff PLC

(57) ABSTRACT

A clip device includes a clip, including a plurality of arms having sliding grooves; and an intermediate member inserted into the sliding grooves for connecting the plurality of arms; a pressing tube accommodating a proximal end portion of the clip; a connection member connecting with an operation wire at a proximal end side and including an engaging portion engaging with the intermediate member; and a locking mechanism for lock the plurality of arms when the clip is pulled toward the proximal end side by a predetermined distance by the connection member, wherein the clip includes a contact portion formed on a side surface of the arm to be in contact with the engaging portion from a direction orthogonal to an axial direction of the intermediate portion for preventing a deformation of the engaging portion when the intermediate portion slides along the sliding groove before the plurality of arms are locked.

20 Claims, 24 Drawing Sheets

(56) References Cited

U.S. PATENT DOCUMENTS

| | | |
|---|---|---|
| 5,766,189 A | 6/1998 | Matsuno |
| 6,814,742 B2 | 11/2004 | Kimura et al. |
| 7,727,247 B2 | 6/2010 | Kimura et al. |
| 7,854,739 B2 | 12/2010 | Satake et al. |
| 8,152,824 B2 | 4/2012 | Kimura et al. |
| 8,157,824 B2 | 4/2012 | Kimura et al. |
| 8,172,859 B2 | 5/2012 | Matsuno et al. |
| 8,348,964 B2 | 1/2013 | Kimura et al. |
| 8,444,660 B2 | 5/2013 | Adams et al. |
| 8,465,501 B2 | 6/2013 | Matsuoka et al. |
| 8,529,585 B2 | 9/2013 | Jacobs et al. |
| 8,672,952 B2 | 3/2014 | Suzuki |
| 9,138,234 B2 | 9/2015 | Li et al. |
| 9,662,113 B2 | 5/2017 | Satake et al. |
| 9,687,248 B2 | 6/2017 | Satake et al. |
| 9,949,740 B2 | 4/2018 | Satake et al. |
| 10,524,801 B2 | 1/2020 | Muyari et al. |
| 10,828,035 B2 | 11/2020 | Maekubo |
| 11,141,166 B2 | 10/2021 | Itoh et al. |
| 11,234,707 B2 | 2/2022 | Yu et al. |
| 2002/0045909 A1 | 4/2002 | Kimura et al. |
| 2005/0143767 A1 | 6/2005 | Kimura et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2015/0305741 A1 | 10/2015 | Satake et al. |
| 2018/0353183 A1 | 12/2018 | Maekubo |
| 2021/0267602 A1 | 9/2021 | Tsuji et al. |

FOREIGN PATENT DOCUMENTS

| | | |
|---|---|---|
| JP | 2002-360589 A | 12/2002 |
| JP | 2006-198388 A | 8/2006 |
| JP | 2009-022776 A | 2/2009 |
| JP | 2010-029629 A | 2/2010 |
| JP | 5750620 B2 | 7/2015 |
| WO | 2020/095427 A1 | 5/2020 |
| WO | 2020/095428 A1 | 5/2020 |
| WO | 2020/122120 A1 | 6/2020 |

OTHER PUBLICATIONS

May 11, 2021 International Search Report issued in International Patent Application No. PCT/JP2021/008932.

Apr. 27, 2021 International Search Report issued in International Patent Application No. PCT/JP2021/009575.

Apr. 19, 2022 International Search Report issued in International Patent Application No. PCT/JP2022/002771.

Jul. 4, 2023 Notice of Allowance issued in Japanese Patent Application No. 2022-031146.

Dec. 15, 2023 Notice of Allowance issued in U.S. Appl. No. 17/584,741.

ENDOSCOPIC TREATMENT DEVICE

CROSS-REFERENCE TO RELATED APPLICATIONS

This is a Continuation of application Ser. No. 17/584,741 filed on Jan. 26, 2022, which claims the benefit of U.S. Provisional Application No. 63/141,620 filed on Jan. 26, 2021, PCT International Application No. PCT/JP2021/008932, filed on Mar. 8, 2021, and PCT International Application No. PCT/JP2021/009575, field on Mar. 10, 2021. The entire disclosure of the prior applications are hereby incorporated by reference herein.

TECHNICAL FIELD

The present disclosure relates to an endoscopic treatment device, more specifically, relates to an endoscopic treatment device including a clip unit for ligating tissues.

BACKGROUND ART

The ligation of tissues by using a clip unit is known as an endoscopic treatment. The clip unit includes a pair of arms. When the pair of arms are pulled by a predetermined amount in a state of grasping the tissues, the pair of arms are locked in a state of firmly tightening the tissues.

The clip unit as a treatment unit is introduced into the body in a state of being mounted on an actuator. The clip unit is indwelled in the body in a state of ligating the tissues such that it is necessary to separate the pair of arms from the actuator after being locked.

The clip unit disclosed in Japanese Patent (Granted) Publication No. 5750620 has a configuration in which proximal end portions of a pair of arms are accommodated in a pressing tube. The proximal end portions of the pair of arms are connected with an operation wire.

When the operation wire is pulled to draw the proximal end portions of the pair of arms outside of the pressing tube by a predetermined amount and then release the connection of the pair of arms and the operation wire, the pair of arms are locked in a closed state. Accordingly, until the proximal end portions of the pair or arms are drawn outside of the pressing tube by the predetermined amount, it is possible to push the operation wire so as to open the pair of arms which are half closed.

SUMMARY

According to an aspect of the present disclosure, a clip device includes a clip including a plurality of arms having sliding grooves respectively; and an intermediate member inserted into the sliding grooves for connecting the plurality of arms; a pressing tube configured to accommodate a proximal end portion of the clip; a connection member configured to connect with an operation wire at a proximal end side and including an engaging portion to engage with the intermediate member; and a locking mechanism configured to lock the plurality of arms when the clip is pulled toward the proximal end side by a predetermined distance by the connection member, wherein the clip further includes a contact portion formed on a side surface of the arm, and the contact portion is configured to be in contact with the engaging portion from a direction orthogonal to an axial direction of the intermediate portion for preventing a deformation of the engaging portion during a process when the intermediate portion slides along the sliding groove before the plurality of arms are locked.

According to another aspect of the present disclosure, an endoscopic treatment device includes a clip including a pair of arms at a distal end side of the clip, the pair of arms being configured to freely open and close; a tubular pressing tube into which at least part of the proximal end side of the clip is inserted; a wire configured to control the open and close of the pair of arms; and a connection member configured to connect the pair of arms and the wire, wherein a tail of the pair of arms includes a snap-fit hole, and a distal end of the connection member engages with the snap-fit hole.

According to a further aspect of the present disclosure, a clip device includes a clip including two arms and an intermediate member inserting through a proximal end portion of the two arms to connect the two arms; and a connection member configured to connect an operation wire and the intermediate member, wherein a distal end portion of the connection member includes an engaging portion configured to engage with the intermediate member, the connection member includes a contact portion extending from the engaging portion to a lateral position of the arms while the contact portion being in contact with the arms from the lateral side in a state in which the engaging portion is engaged to the intermediate member, and a width of the contact portion is larger than a width of other portions of the connection member.

BRIEF DESCRIPTION OF DRAWINGS

FIG. 9 is not a view showing the present endoscopic treatment device.

DESCRIPTION OF EMBODIMENTS

An embodiment of the present disclosure is described by referring to FIG. 1 to FIG. 9.

Figure 1:
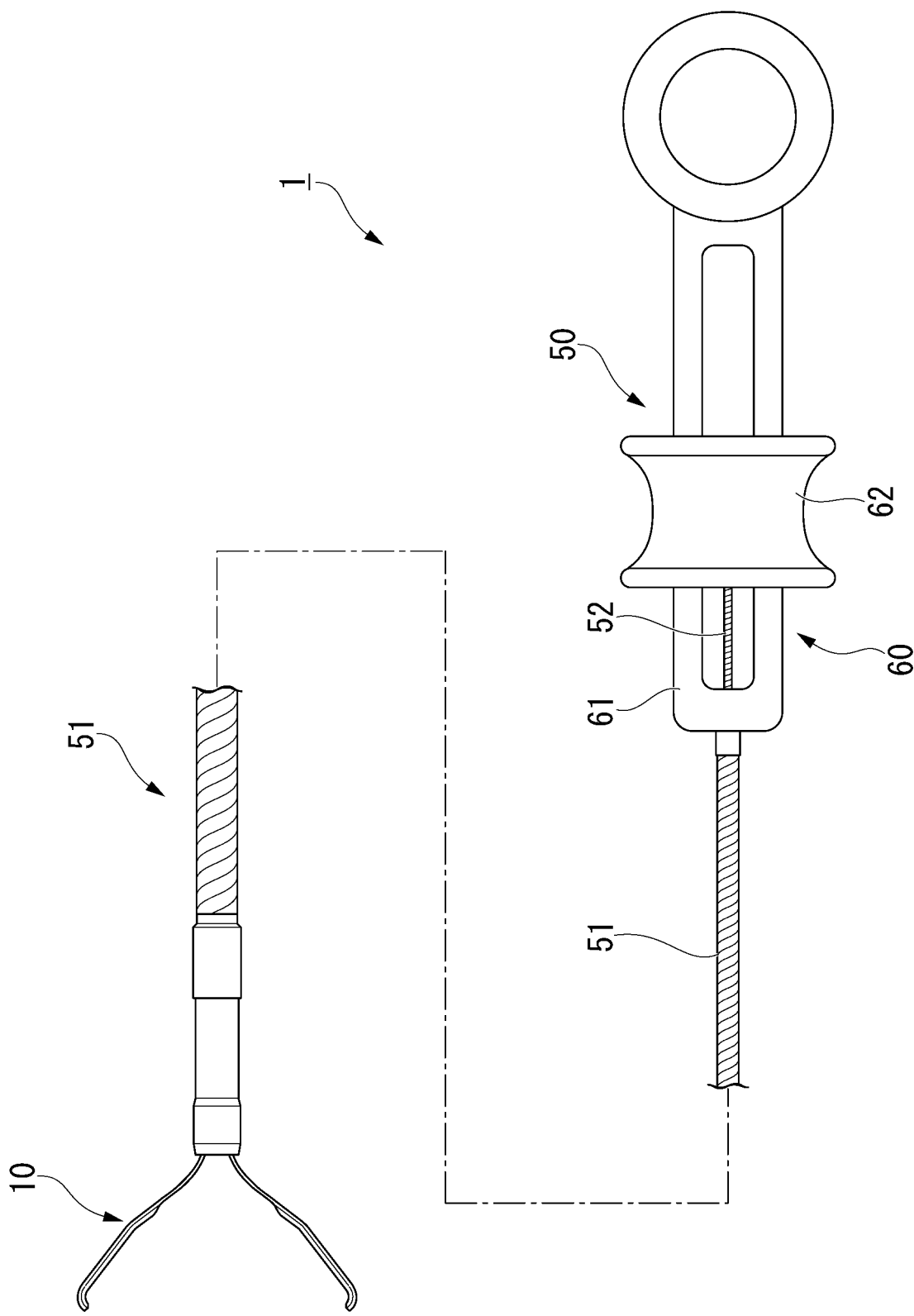
FIG. 1 is a view showing an overall configuration of an endoscopic treatment device according to a first embodiment of the present disclosure.

FIG. 1 is a view showing an exterior appearance of an endoscopic treatment device 1 according to the present embodiment. The endoscopic treatment device 1 includes a clip unit 10 that is indwelled in the body and an applicator 50 configured to operate the clip unit 10. The clip unit 10 is attached to a tip end (distal end) of the applicator 50.

Figure 2:
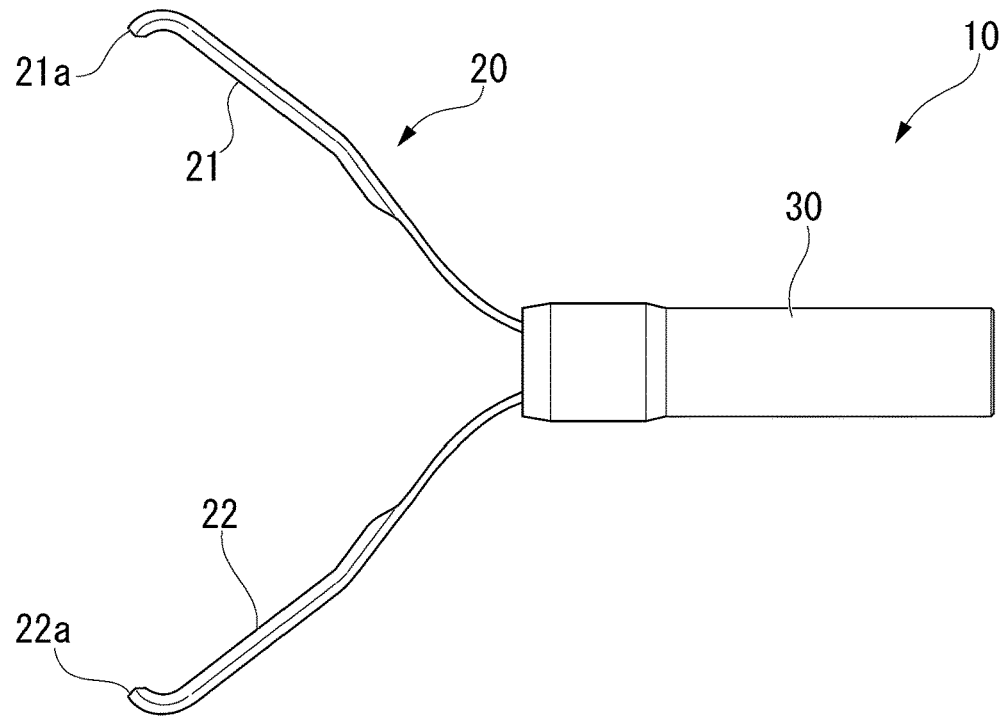
FIG. 2 is a view showing a clip unit of the endoscopic treatment device.
Figure 3:
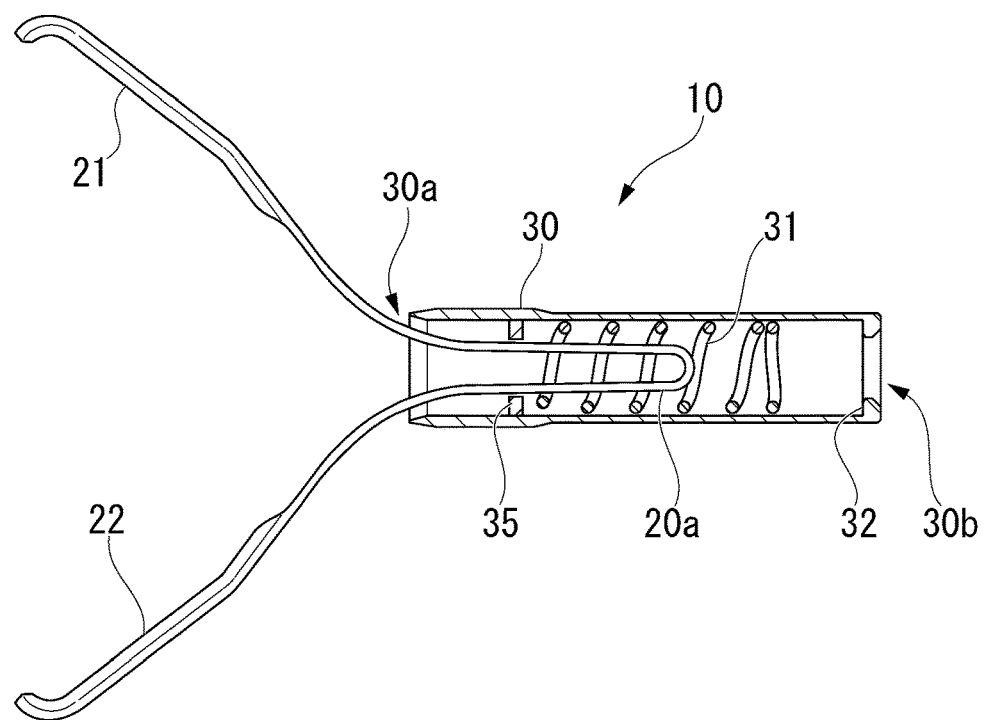
FIG. 3 is a cross-sectional view showing the clip unit.

FIG. 2 is a view showing an exterior appearance of the clip unit 10. FIG. 3 is a cross-sectional view of the clip unit 10. As shown in FIG. 2, the clip unit 10 includes an arm portion 20 and a pressing tube (tubular member) 30 in which part of the arm portion 20 is accommodated.

The arm portion 20 includes a pair of arms as a first arm 21 and a second arm 22. The first arm 21 and the second arm 22 include a claw 21a and a claw 22a at the distal end portions respectively. As shown in FIG. 3, the first arm 21 and the second arm 22 are connected with each other at a proximal end portion 20a of the arm portion 20. The proximal end portion 20a is formed in a U-shape.

The arm portion 20 is made of an alloy material or a metal material. Examples of the material of the arm portion 20 include the stainless steel, the cobalt-chromium alloy, the nickel-titanium alloy, and the like.

The first arm 21 and the second arm 22 are expanded to be open in an initial state as shown in FIG. 2. The first arm 21 and the second arm 22 are configured to generate a biasing force to return to the initial state due to the elastic force of the material when the first arm 21 and the second arm 22 approach each other from the initial state.

The pressing tube 30 is a tubular member made of a metal material, a resin or the like. As shown in FIG. 3, the proximal end portion 20a of the arm portion 20 is accommodated in the pressing tube 30. The distal end portion of the arm portion 20 is configured to protrude from a distal end opening 30a of the pressing tube 30. A proximal end opening 30b of the pressing tube 30 is smaller than the distal end opening 30a.

Figure 4:
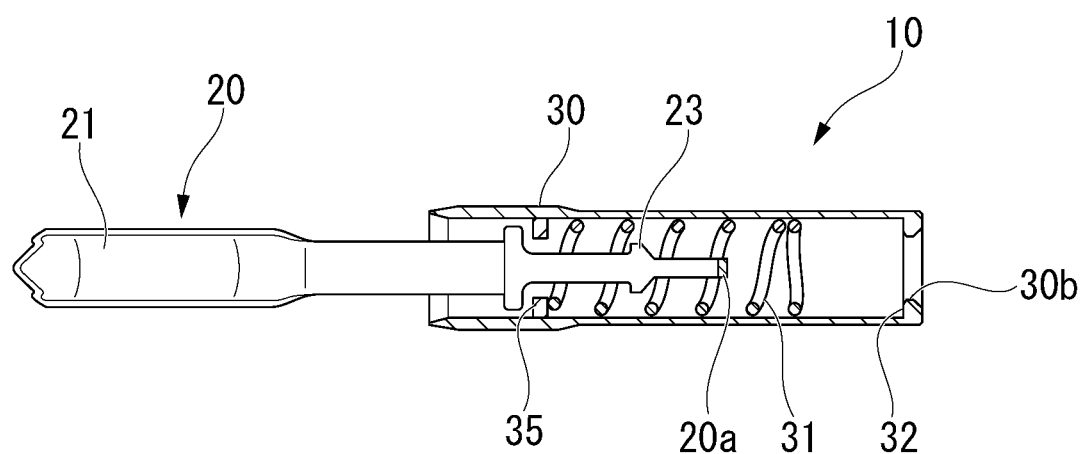
FIG. 4 is a cross-sectional view showing the clip unit from a different direction from that in FIG. 3.

FIG. 4 is a view showing the interior of the pressing tube 30 that is viewed from a different direction from that in FIG. 3. As shown in FIG. 4, a locking portion 23 is provided in an intermediate portion of each arm of the arm portion 20, and a dimension of each arm 21, 22 in the width direction at the locking portion 23 is large (only the first arm 21 can be viewed in FIG. 4). Each locking portion 23 can pass through the proximal end opening 30b when the first arm 21 and the second arm 22 approach each other. When the first arm 21 and the second arm 22 separate from each other after passing through the proximal end opening 30b, the locking portion 23 cannot pass through the proximal end opening 30b. As a result, the arm portion 20 is locked in a state in which the pair of arms are closed.

A coil spring 31 is disposed inside the pressing tube 30. A proximal end of the coil spring 31 is able to come into contact with a proximal end surface 32 of the pressing tube 30 including the proximal end opening 30b.

A washer 35 is disposed at the distal side of the coil spring 31. An inner diameter of the washer 35 is smaller than the inner diameter of the coil spring 31. The distal side of the first arm 21 and the second arm 22 are larger in the width than that of the proximal end portion and the distal end side of the first arm 21 and the second arm 22 has the dimension that is impossible to enter the washer 35. Accordingly, the washer 35 has the configuration to be in contact with the distal side rear surface of the first arm 21 and the second arm 22 such that the distal side of the first arm 21 and the second arm 22 does not enter the coil spring 31 without providing an end coil portion having a small inner diameter in the coil spring 31.

For example, part of the above-described configuration of the arm portion 20 and the pressing tube 30 is known and disclosed in PCT International Publication No. WO 2014/181676; however, it is possible to apply the following modifications to the configuration.

The opening width of the arm portion 20 in the initial state may be appropriately changed by changing a bending angle (curvature radius) between a region inside the pressing tube 30 and a region outside the pressing tube 30 in the initial state. At this time, by decreasing the curvature radius, it is possible that the restoration property to the initial state will be reduced; however, it is possible to prevent the reduction by changing the plate thickness of the arm portion. Furthermore, it is possible to provide multiple variations with different opening widths in the initial state by only changing the curvature radius and using the same member.

For example, the arm portion can be manufactured by punching and bending a metal plate material; however, it is possible to chamfer the edge portion in contact with the internal surface of the pressing tube after the manufacturing so as to make the movement inside the pressing tube 30 to be smooth and prevent the wear and the damage to the pressing tube by the edge portion.

As shown in FIG. 1, the applicator 50 includes an elongated insertion portion 51, an operation wire (power transmission member) 52 inserted through the insertion portion 51, and an operation portion 60 connected to the insertion portion 51.

The structure of the distal end side of the insertion portion 51 will be described below, with regard to the portion other than the distal end portion, for example, it is possible to adopt a sheath formed from a coil. In the case of using the coil sheath, it is preferable to process the distal and proximal end surfaces to be flat by the polishing procedure or the like.

The operation portion 60 includes a main body 61 connected with the insertion portion 51, and a slider 62 attached to the main body 61 to be slidable with respect to the main body 61.

As the operation wire 52, it is possible to adopt a twisted wire made of the metal wire, for example. The proximal end portion of the operation wire 52 is connected to the slider 62. When the slider 62 is moved with respect to the main body 61, it is possible to advance and retract the operation wire 52 in the insertion portion 51.

The connection aspect of the operation wire 52 and the slider 62 is appropriately determined, and an example will be described referring to FIG. 5.

At first, a block 101 including a penetration horizontal hole 101a and a bottomed vertical hole 101b communicating with the horizontal hole 101a is prepared. As shown in the part (a) of FIG. 5, the operation wire 52 passing through the pipe 102 for preventing the buckling is made to pass the horizontal hole 101a.

Figure 5:
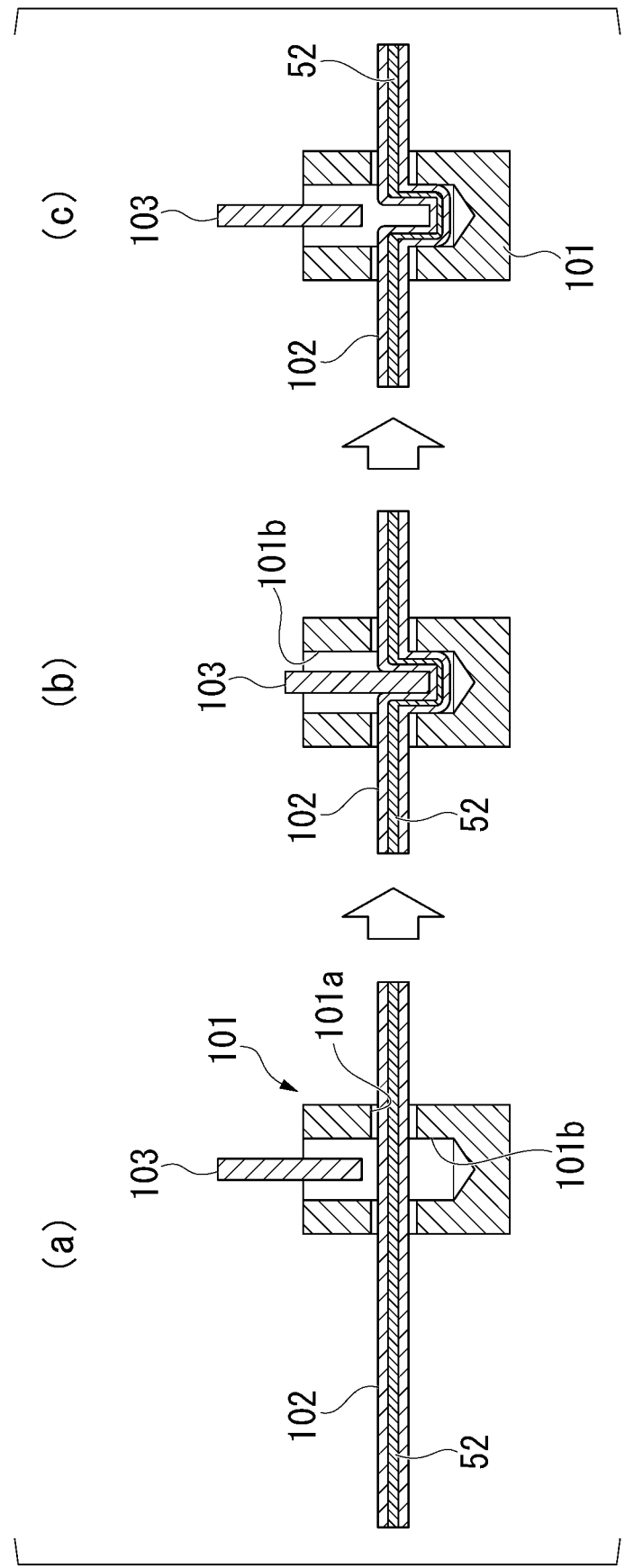
FIG. 5 is a view showing connection procedures of a slider and a wire.

As shown in the part (b) of FIG. 5, when the pin 103 is inserted into the vertical hole 101b and then the pipe 102 and the operation wire 52 are pressed toward the bottom of the vertical hole 101b to perform the caulking, part of the pipe 102 and the operation wire 51 are bent to enter the vertical hole 101b. As a result, as shown in the part (c) of FIG. 5, even the pin 103 is removed, it is impossible for the pipe 102 and the operation wire 52 to slip out from the block 101 such that the pipe 102 and the operation wire 52 are fixed to the block 101.

Thereafter, it is possible to connect the pipe 102 and the operation wire 52 to the slider 62 by assembling the block 101 to the slider 62.

Figure 6:
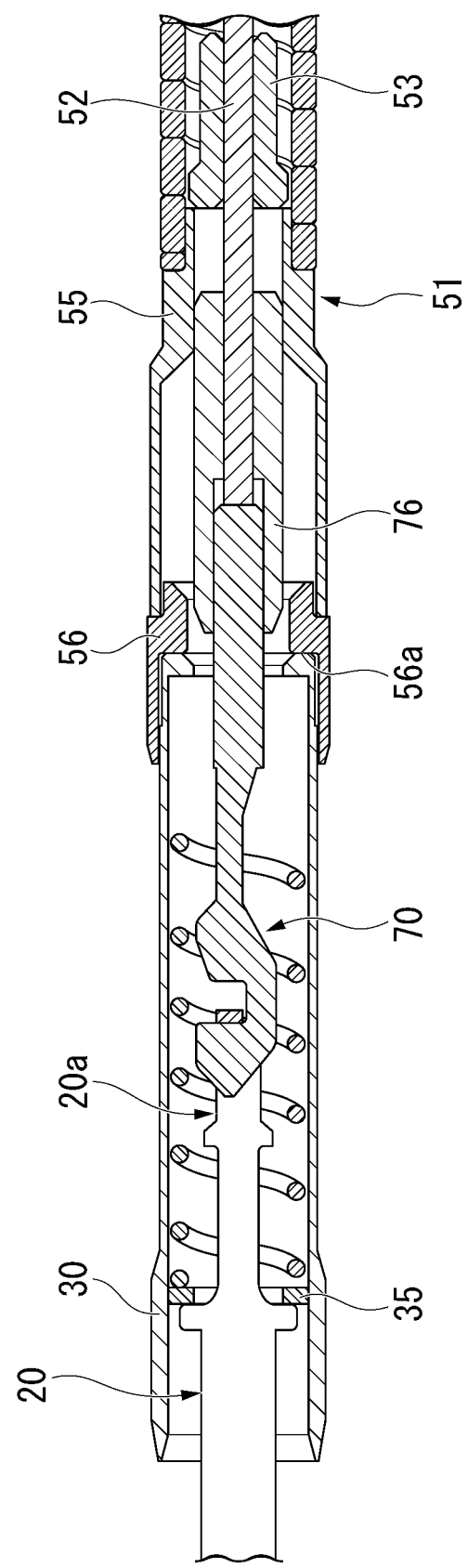
FIG. 6 is an enlarged cross-sectional view showing a portion of the endoscopic treatment device for mounting the clip thereto.

FIG. 6 is an enlarged view showing the distal end portion of the applicator 50 to which the clip unit 10 is attached. The clip unit 10 and the applicator 50 are detachably connected to each other by the hook (engaging portion) 70 disposed at the distal end of the operation wire 52 engaging with the proximal end portion (engaged portion) 20a of the arm portion 20.

The distal end portion of the insertion portion 51 includes a tubular first member 55 and a tubular second member 56 attached to the distal side of the first member 55.

The outer diameter of the proximal portion of the second member 56 is smaller than the inner diameter of the first member 55, and the second member 56 is connected to the first member 55 by welding or the like in a state of entering the first member 55. The inner diameter of the distal side of the second member 56 is larger than the outer diameter of the pressing tube 30 and the proximal portion of the pressing tube 30 enters the second member 56. The inner diameter of the proximal side of the second member 56 is smaller than that of the distal side of the second member 56 such that the second member 56 is formed in the structure in which a step surface 56a is generated due to the difference of the diameters and the step surface 56a can support the proximal portion of the pressing tube 30.

The hook 70 passes through the inside of the first member 55 and the second member 56 to enter the pressing tube 30 and the hook 70 is engaging with the proximal end portion 20a of the arm portion 20 inside the pressing tube 30.

The hook 70 is attached to a connection member 76 fixed to the distal end of the operation wire 52 by the brazing or the like.

Figure 7:
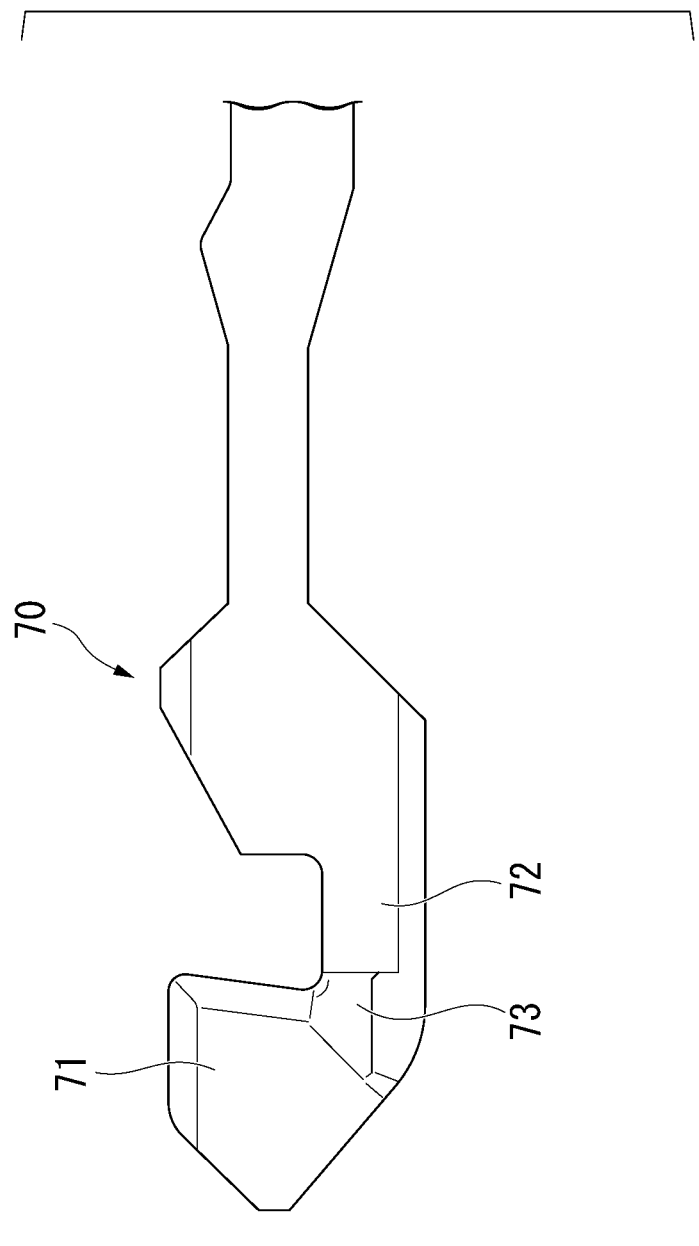
FIG. 7 is an enlarged view of a hook.
Figure 7:
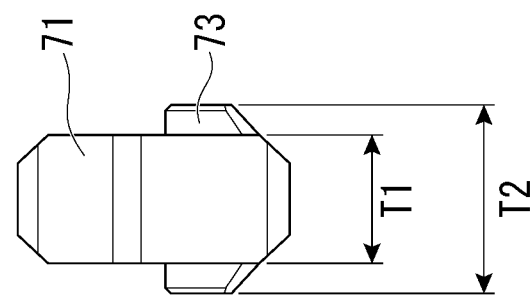

FIG. 7 is an enlarged view showing the hook 70. The left side of FIG. 7 is a front view of the hook 70, and the right side thereof is the right-side view of the hook 70. The distal side of the hook 70 includes a hook portion 71 locked to the arm portion 20, a support portion 72 extending backwardly from the hook portion 71, and a protrusion portion 73 formed at the boundary portion of the hook portion 71 and the support portion 72. The support portion 72 is generally parallel to the operation wire 52, and there is an approximately right angle formed between the proximal surface 71a of the hook portion 71 and the extending direction of the support portion 72.

Figure 8:
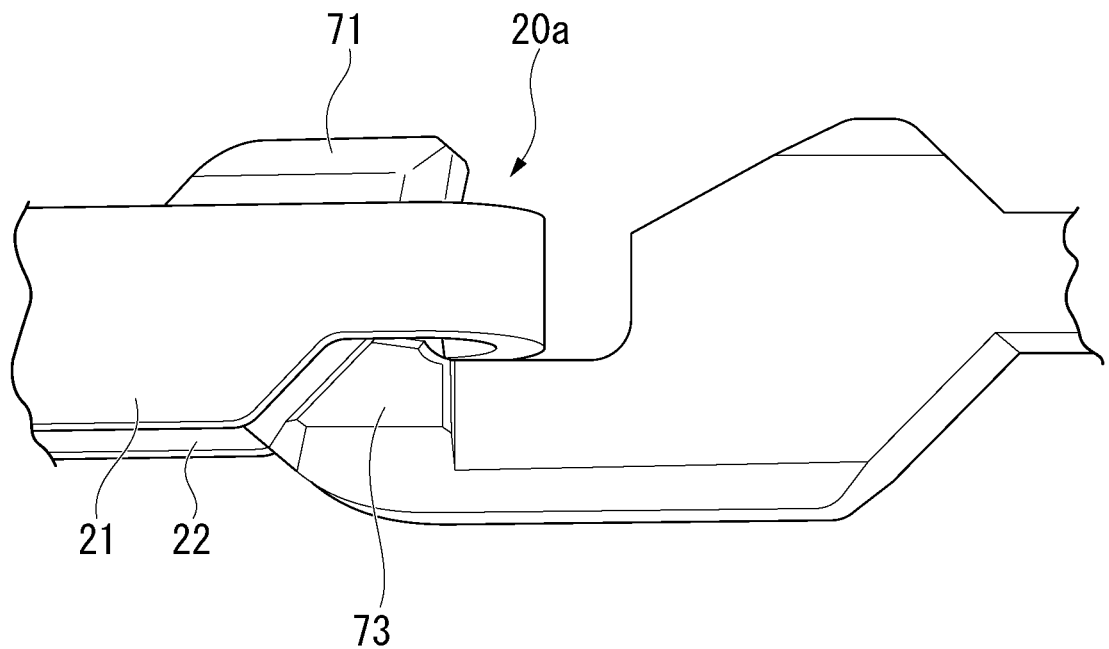
FIG. 8 is an enlarged view showing an engagement portion of the hook and the arm portion.

The hook portion 71 and the support portion 72 has approximately the same thickness (the thickness T1 shown in FIG. 7); however, the thickness of the protrusion portion 73 is the thickness T2 that is larger than the thickness T1. The distance between the first arm 21 and the second arm 22 in the proximal end portion 20a of the arm portion 20 is equal to or larger than the thickness T1 and less than the thickness T2. Accordingly, as shown in FIG. 8, the hook portion 71 enters the space between the first arm 21 and the second arm 22 to be locked to the proximal end portion 20a. On the other side, the protrusion portion 73 interferes with the first arm 21 and the second arm 22 such that the protrusion portion 73 cannot enter the space between the first arm 21 and the second arm 22.

The hook 70 having the above-described shape can be manufactured by using the plate material having the thickness T2 to perform the forging procedure, the Metal Injection Mold (MIM) procedure or the like.

A stopper 53 is attached to the operation wire 52. The shape and the dimension of the stopper 53 are determined to be impossible to enter the first member 55 such that when the stopper 53 comes into contact with the proximal end of the first member 55, the operation wire 52 cannot advance any further. The exterior surface of the stopper 53 is chamfered such that it is difficult for the operation wire 52 to interfere with the insertion portion 51 when the operation wire 52 is advanced and retracted in the insertion portion 51.

The operations when the endoscopic treatment device 1 having the above-described configuration is used will be described. The endoscopic treatment device 1 is introduced into the body through the channel of the endoscope. When the user inserts the endoscopic treatment device 1 into the endoscope, the user retracts the slider 62 by a predetermined amount so as to insert the arm portion 20 in a state in which the arm portion 20 is closed and the arm portion 20 is not locked. The clip unit 10 in which the arm portion 20 is closed and the distal end portion of the insertion portion 51 may be inserted into the endoscope in a state of being accommodated in an outer sheath that is separately prepared.

When the user protrudes the endoscopic treatment device 1 from the opening of the channel of the distal end portion of the endoscope and then reduces the force pulling the slider or retracting the outer sheath, the arm portion 20 advances with respect to the pressing tube 30 due to the elastic restoration force of the arm portion 20 itself and the elastic restoration force of the coil spring 31. As a result, the pair of arms 21, 22 enter the open configuration in which the pair of arms 21, 22 are open. When the stopper 53 comes into contact with the proximal end of the first member 55, the arm portion 20 cannot advance with respect to the pressing tube 30 such that the open configuration is maintained and the arm portion 20 does not slip out from the pressing tube 30.

If the outer sheath is too short, when the outer sheath is retracted, the endoscopic treatment device 1 advances powerfully due to the above-described elastic restoration force such that it is preferable to adopt the outer sheath with the length (for example, approximately 30 millimeters) slightly shorter than the length of the insertion portion 51.

When the user retracts the slider 62 with respect to the main body 61, the operation wire 52 and the hook 70 are pulled and the arm portion 20 is retracted with respect to the pressing tube 30. As a result, the pair of arms 21, 22 enters the closed configuration in which the pair of arms 21, 22 are closed. The user positions the tissues between the pair of arms 21, 22 and then close the pair of arms 21, 22 to ligate the tissues. Until the locking operation described below is performed, by advancing the slider 62 with respect to the main body 61, it is possible to transition the pair of arms 21, 22 from the closed configuration to the open configuration. Accordingly, according to the endoscopic treatment device 1, until the locking operation is performed, it is possible to re-grasp the tissues by operating the clip unit using the operation wire 52.

Within the movement range of the operation wire 52 where the re-grasp operation is able to perform, at least part of the distal side of the hook 70 is positioned at the proximal side inside the second member 56 where the inner diameter is small such that it is impossible that the engagement of the hook 70 and the proximal end portion 20a is released between the re-grasp operation.

When it is determined that it is suitable to ligate the tissues positioned between the pair of arms 21, 22, the user performs the locking operation for fixing the closed state of the arm portion 20. During the locking operation, the user further retracts the slider 62 with respect to the main body 61 to exceed the range where it is possible to perform the re-grasp operation. When the slider 62 is retracted, the operation wire 52 is pulled and the pair of arms 21, 22 becomes approximately parallel to each other while grasping the tissues to enter the pressing tube 30. Furthermore, the locking portions 23 provided in the pair of arms 21, 22 approach each other to become the positional relationship capable of passing through the proximal end opening 30b of the pressing tube 30.

The pair of locking portions 23 passing through the proximal end opening 30b and moving to the outside of the pressing tube 30 separates from each other to become the positional relationship that is impossible to pass through the proximal end opening 30b again. As a result, the pair of locking portions 23 come into contact with the proximal end surface of the pressing tube 30 so as to prevent the arm portion 20 from protruding from the pressing tube 30 and the arm portion 20 is locked to maintain the closed configuration.

When the user further retracts the slider 62, the arm portion 20 further retracts and the locking portion 23 passes through the proximal end opening 30b to move to the outside of the pressing tube 30. Furthermore, the locking portion 23 is locked to the proximal end surface of the pressing tube 30 and the arm portion 20 is locked to be unable to open.

When the user further retracts the slider 62, the distal side of the hook 70 deforms due to the retraction force. For example, the hook portion 71 deforms such that the proximal surface 71a and the support portion 72 enters a state to be approximately parallel to each other or the support portion 72 deforms such that the hook portion 71 rotates around the support portion 72 as a rotation center.

As a result, the engagement of the hook 70 and the proximal end portion 20a is released and the pressing tube 30 is separated from the second member 56 such that the clip unit 10 is indwelled in the tissues.

When the user removes the endoscope and the applicator 50 to the outside of the body, the series of procedures are finished.

In the endoscopic treatment device 1, after the arm portion 20 is locked, it is possible to release the engagement between the arm portion 20 and the hook 70 by further retracting the hook 70 only such that basically, there is no case in which the hook 70 advances after the arm portion 20 is locked. However, in the case in which the user does not notice that the arm portion 20 has been locked and tries to perform the re-grasp operation, it is possible that the hook 70 is operated to advance. At this time, even the hook 70 is operated to advance, since the arm portion 20 cannot advance, it is possible that the longitudinal direction of the arm portion and the longitudinal direction of the hook are not parallel to each other.

Figure 9:
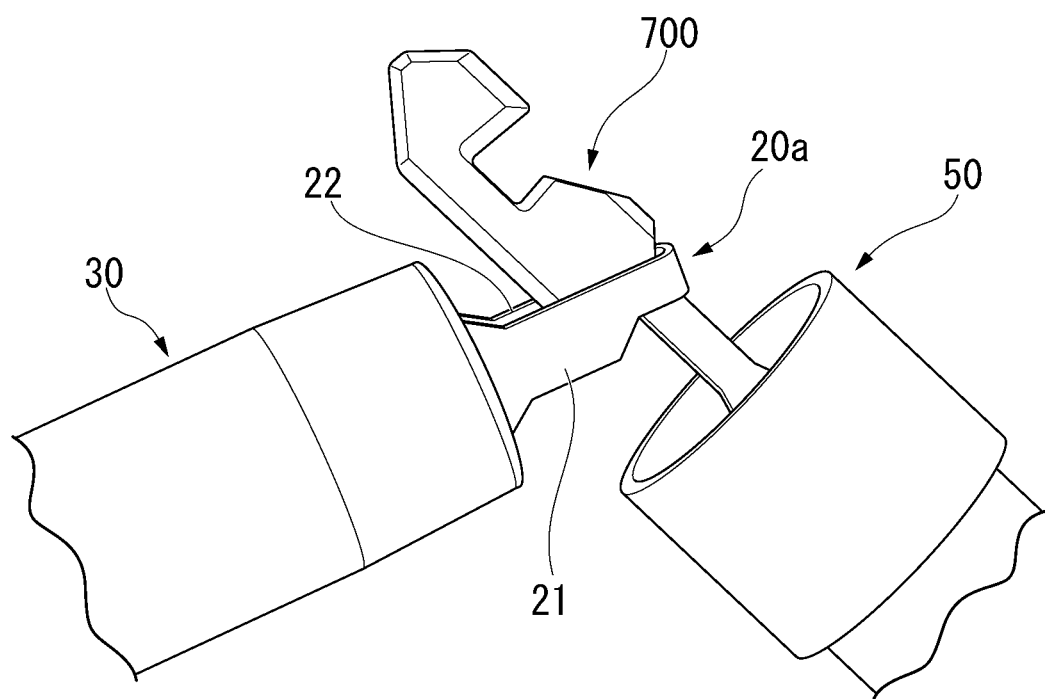
FIG. 9 is a view showing a state in which it is difficult to release the connection of the hook and the arm portion.

In this case, as shown in FIG. 9, after consideration, the inventor finds that it is possible that the advanced hook 700 (this hook is not the hook included in the endoscopic treatment device 1) may enter the space between the first arm 21 and the second arm 22 in the proximal end portion 20a of the arm portion. Furthermore, in the state as shown in FIG. 9, it is known that it becomes significantly difficult to separate the hook 70 from the proximal end portion 20a.

The inventor further studies with the configuration and successes in eliminating the possibility by providing the protrusion portion 73 in the hook 70, wherein the protrusion portion 73 has the dimension and the size that is unable to enter the space between the first arm 21 and the second arm 22. Accordingly, even the user accidentally advances the hook 70 after the arm portion 20 is locked, the protrusion portion 73 interferes with the proximal end portion 20a so as to be unable to enter the space between the first arm 21 and the second arm 22 and the state as shown in FIG. 9 can be definitely prevented.

As described above, according to the endoscopic treatment device 1 described in the present embodiment, it is possible to realize the re-grasping operation of the tissues by the clip unit 10 while releasing the connection of the applicator 50 and the clip unit 10 by pulling the operation wire 52 only such that the operations become easy. Furthermore, as described above, it is possible to definitely prevent the situation in which it becomes difficult to release the connection of the applicator 50 and the clip unit 10 due to the operations after the arm portion is locked.

In the endoscopic treatment device 1, the first member 55 having the large inner diameter and the second member 56 having the small inner diameter are attached to the distal end of the insertion portion 51. Accordingly, it is possible to definitely support the pressing tube 30 by the second member 56 while applying the force with the necessary amount to the arm portion for the locking operations. As described above, when the two end surfaces of the coil sheath are processed to be flat, the force with the large amount can be stably received by the applicator 50 such that the support becomes further stable.

Furthermore, until the arm portion 20 is locked, the hook 70 is positioned in the portion proximal to the second member 56 where the inner diameter is further narrower such that the large displacement of the hook 70 due to the deformation is prevented and the connection state with the arm portion 20 is definitely maintained.

Additionally, after the arm portion 20 is locked, the hook 70 is positioned in the large space inside the first member 55 such that the space suitable for the large displacement due to the deformation is secured. As a result, it is possible to smoothly release the connection of the arm portion and the hook by the traction of the operation wire 52.

Hereinbefore, one embodiment of the present disclosure has been described; however, the scope of the present disclosure is not limited to the above-described embodiment. Configurations can be added, omitted, replaced, and other modifications without departing from the spirit of the present invention. Hereinafter, several changes will be described as examples, however, other changes are possible to be applied. Two or more of these changes may be combined as appropriate.

Figure 10:
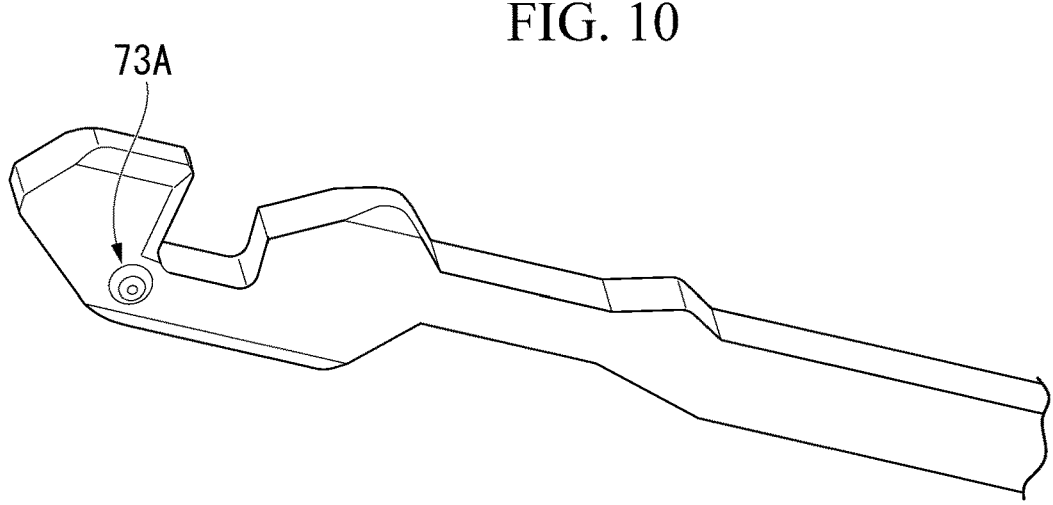
FIG. 10 is a view showing a modification example of the hook.

The aspect of the protrusion portion is not limited to the above-described configuration. The protrusion portion 73A provided in the hook according to the modification example as shown in FIG. 10 is configured to protrude to only one side in the width direction (the thickness direction of the plate-shaped material). The protrusion portion 73A may be formed by applying an impact such as the punch or the like from the opposite side besides the above-described forging and the MIM. In the case of forming the protrusion portion 73A by the punch or the like, the opposite side of the protrusion portion 73A becomes the concave portion such that there may be a case in which the thickness T2 of the protrusion portion 73A is not larger than the distance between the first arm and the second arm; however, the same effect can be achieved once the protrusion portion 73A protrudes enough on the surface at one side.

Figure 11:
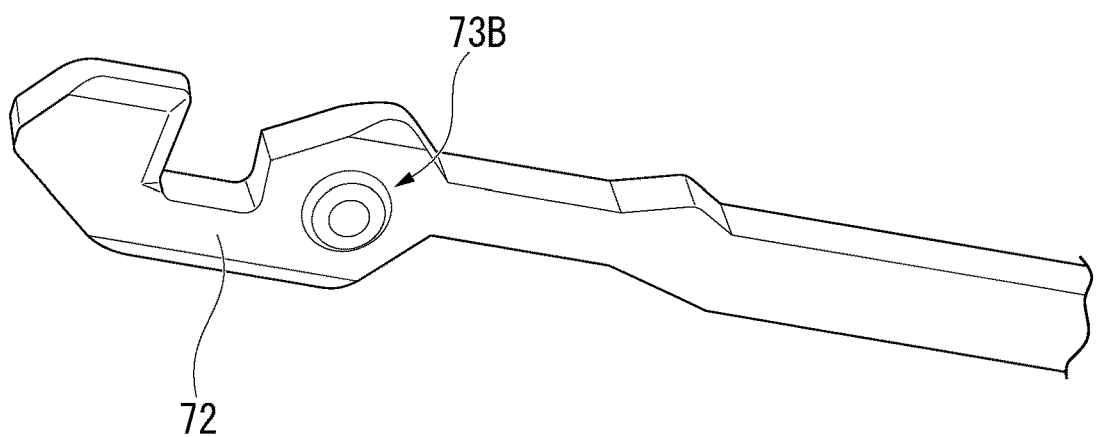
FIG. 11 is a view showing a modification example of the hook.

The position for disposing the protrusion portion may be changed. The protrusion portion 73B disposed in the hook according to the modification example as shown in FIG. 11 is positioned at the proximal side of the support portion 72. Even in such a configuration, it is possible to prevent the whole hook from entering the space between the first arm and the second arm.

The power transmission member according to the present disclosure is not limited to the above-described wire. For example, in a case in which the present disclosure is applied to the treatment device used with the laparoscope, the power transmission member may be a rigid rod.

In the endoscopic treatment device according to the present disclosure, the structure of the engaging portion and the engaged portion may be reversed. For example, the hook may be disposed at the proximal end portion of the arm portion, and the structure in a U-shape or a loop shape that is engageable with the hook may be disposed at the distal end portion of the operation wire.

Figure 13:
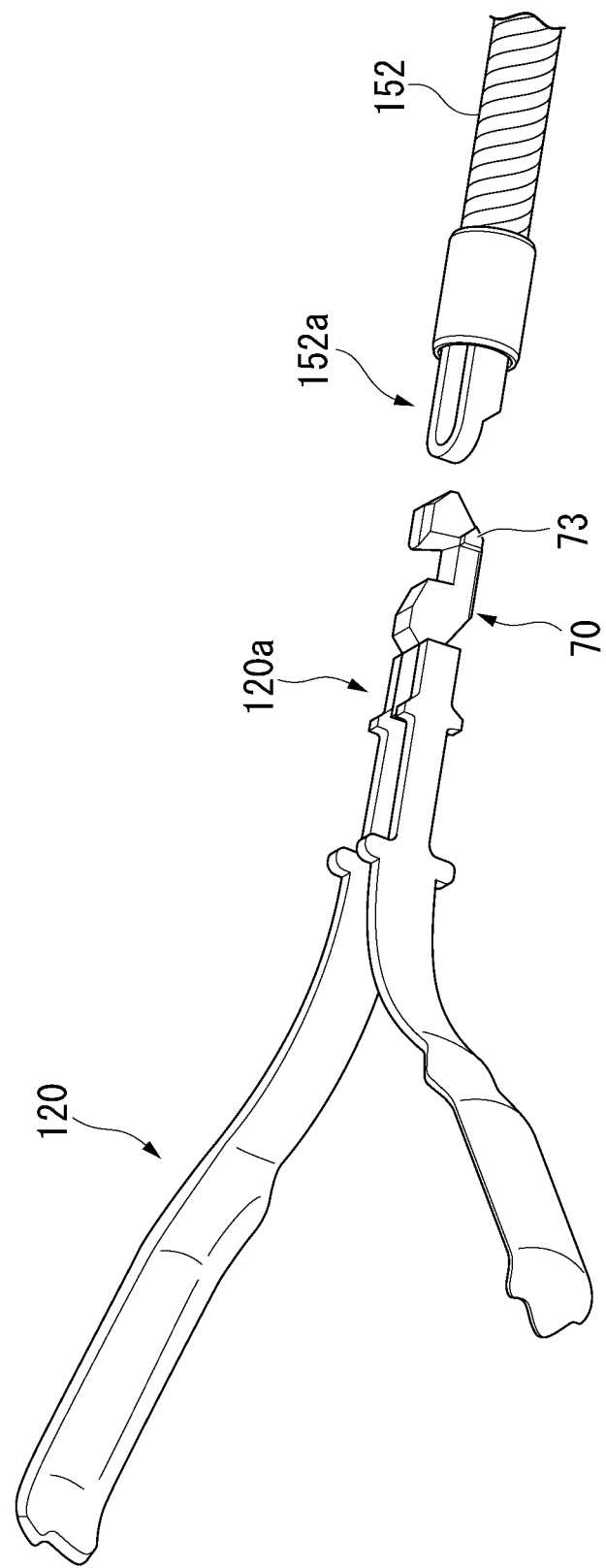
FIG. 13 is a view showing an engagement portion of the hook and the arm portion in a modification example.

The modification example of the arm portion and the operation wire in which the structure of the engaging portion and the engaged portion is reversed is shown in FIG. 13. As shown in FIG. 13, the hook 70 having the protrusion portion 73 is disposed in the proximal end portion 120a of the arm portion 120, and the hook 70 is engaged with the U-shaped engaged portion 152a disposed at the distal end of the operation wire 152. The same effect with the above-described embodiment may be achieved by such a configuration.

In the endoscopic treatment device according to the present disclosure, the structure configured to attach a new clip unit to perform the indwell procedures again after indwelling the clip unit may be applied. In this case, the configuration in which the hook is elastically deformed to release the connection with the arm portion, or as described above, the configuration in which the structure of the engaging portion and the engaged portion is reversed is preferable. The structure as shown in FIG. 13 is suitable for the case of adopting the structure in which the hook is plastic deformed to release the connection while it is possible to reload a new clip unit.

Figure 12:
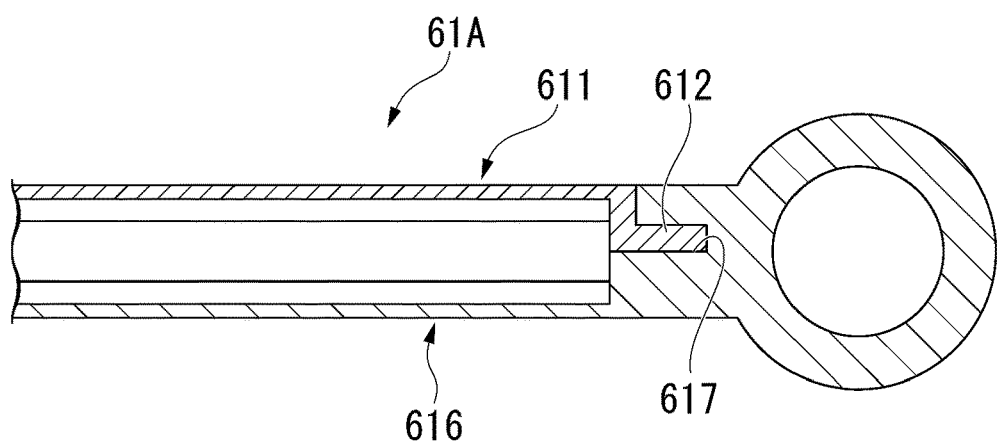
FIG. 12 is a view showing a modification example of an operation portion main body.

In the endoscopic treatment device according to the present disclosure, when the connection of the applicator and the clip unit is released, the large force is applied to the main body 61 of the operation portion 60. For example, the main body 61 may be formed by integrating two members by snap-fitting or the like, wherein the two members have a shape obtained by dividing a cylinder made of resin or the like into half. At this time, similar to the main body 61A according to the modification example as shown in FIG. 12, the protrusion 612 is provided in the first half-divided member 611, and once the first half-divided member 611 and the second half-divided member 616 are integrated in the state in which the protrusion 612 enters the concave portion 617 provided in the second half-divided member 616, it is possible to prevent the first half-divided member 611 and the second half-divided member 616 from being unintentionally separated from each other when the large force is applied to the main body.

Second Embodiment

Figure 14:
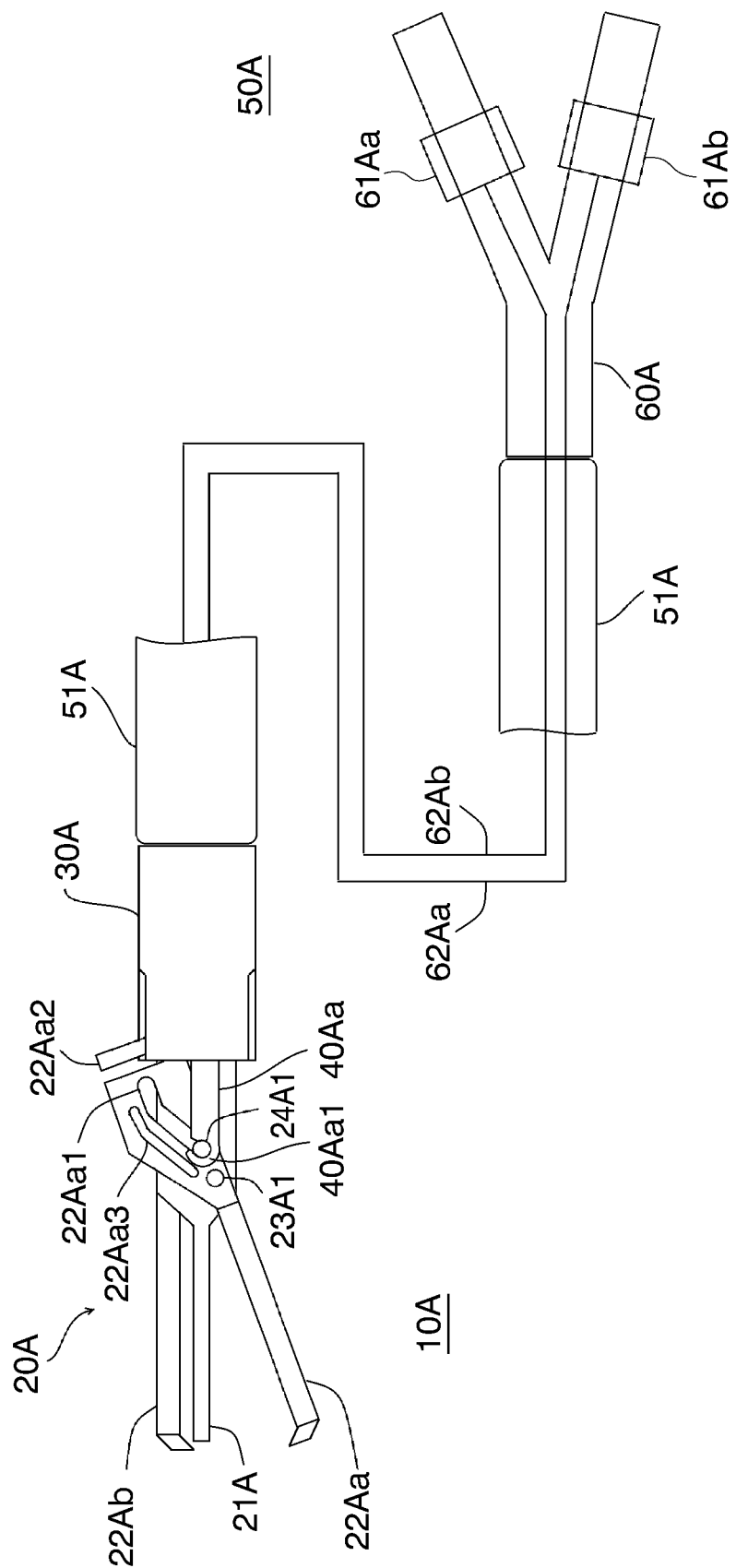
FIG. 14 is a side view schematically showing a clip device according to a second embodiment.

The endoscopic treatment device according to the present embodiment is a clip device. As shown in FIG. 14, the clip device includes a clip unit 10A indwelled in the body and an applicator 50A configured to operate the clip unit 10A.

The clip unit 10A includes a clip 20A and a pressing tube 30A configured to accommodate part of the clip 20A.

The clip 20A includes a fixed arm 21A positioned at the center and two movable arms 22Aa, 22Ab positioned at two sides of the fixed arm 21A. The movable arms 22Aa, 22Ab are configured to be able to open and close independently from the fixed arm 21A.

The movable arm 22A is connected to the fixed arm 21A by a first pin 23A1 to be rotatable. A first sliding groove 22Aa1 is provided in the proximal end portion of the movable arm 22Aa. A second pin 24A1 is inserted into the first sliding groove 22Aa1. The second pin 24A1 is connected to a first hook claw 40Aa1 (first engaging portion) of a first connection member 40Aa.

Figure 15A:
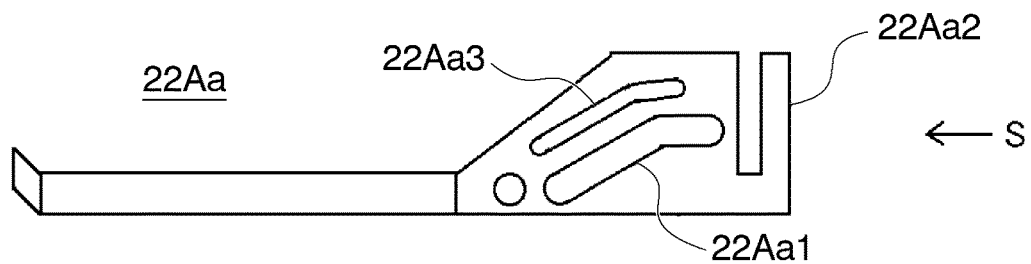
FIG. 15A is a side view showing a first connection member according to the second embodiment.
Figure 15B:
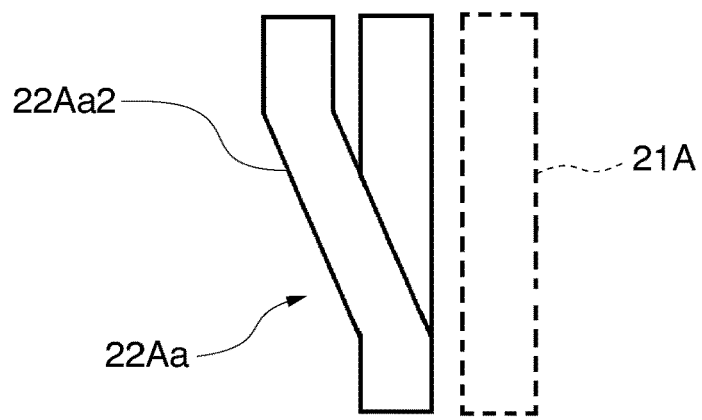
FIG. 15B is a view showing the first connection member viewed from a direction indicated by the arrow S shown in FIG. 15A.

A protrusion portion 22Aa2 for locking the clip 20A is provided in the proximal end portion of the movable arm 22Aa. FIG. 15A is the side view of the movable arm 22Aa. In FIG. 15A, the protrusion portion 22Aa2 extends along the direction orthogonal to the longitudinal direction of the movable arm 22Aa. FIG. 15B is the view of observing the movable arm 22Aa from the direction indicated by the arrow S in FIG. 15A. In FIG. 15B, in the case in which there is no external force is applied, the protrusion portion 22Aa2 extends diagonally in the direction separating away from the fixed arm 21A. The protrusion portion 22Aa2 is able to elastically deform in the direction of approaching the fixed arm 21A.

Figure 16:
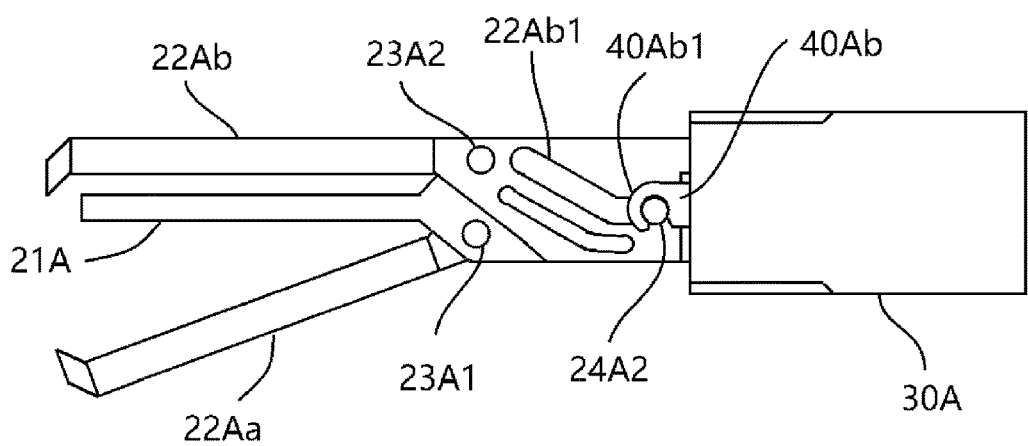
FIG. 16 is a side view showing a clip unit of the clip device according to the second embodiment which is viewed from an opposite side surface from the side surface shown in FIG. 14.

As shown in FIG. 16, the movable arm 22Ab is connected to the fixed arm 21A by a third pin 23A2 to be rotatable. A second sliding groove 22Ab1 is provided in the proximal end portion of the movable arm 22Ab. A fourth pin 24A2 is inserted into the second sliding groove 22Ab1. The fourth pin 24A2 is connected to a second hook claw 40Ab1 (second engaging portion) of a second connection member 40Ab. A protrusion portion 22Ab2 for locking the clip 20A is provided in the proximal end portion of the movable arm 22Ab. The structure of the protrusion portion 22Ab2 is the same with that of the protrusion portion 22Aa2, and the duplicate description will be omitted.

Figure 17A:
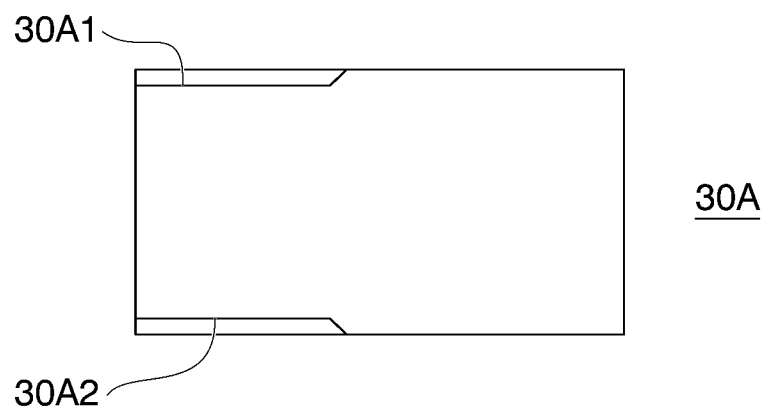
FIG. 17A is a side view showing a pressing tube.
Figure 17B:
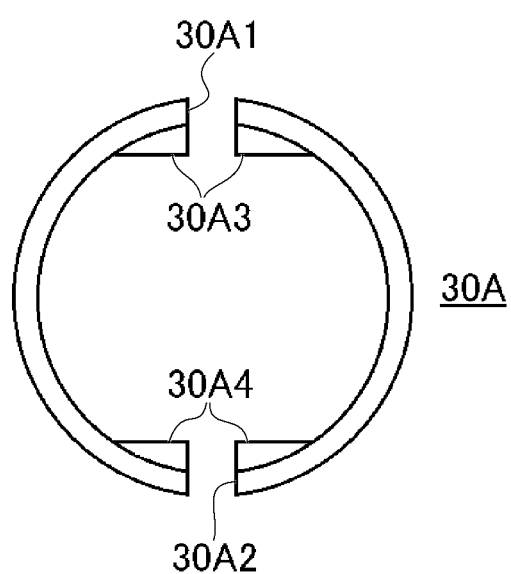
FIG. 17B is a view observing the pressing tube along an axial direction of the pressing tube.

The pressing tube 30A is configured to accommodate the proximal end portion of the fixed arm 21A and the proximal end portions of the movable arms 22Aa, 22Ab. As shown in FIG. 17A, two groove portions 30A1, 30A2 opposite to the circumferential direction of the pressing tube 30A are provided at the distal end of the pressing tube 30A. When the movable arms 22Aa, 22Ab are open and closed, the movable arms 22Aa, 22Ab pass through the groove portions 30A1, 30A2, respectively. As shown in FIG. 17B, inside the pressing tube 30A, stopper portions 30A3, 30A4 being able to contact with the above-described protrusions 22Aa2, 22Ab2 are provided in the edge portions of the groove portions 30A1, 30A2. The stopper portions 30A3, 30A4 form the flat stopper surfaces in the edge portions of the groove portions 30A1, 30A2.

The protrusion portions 22Aa2, 22Ab2 are configured to be unable to come out from the groove portions 30A1, 30A2 after contacting with the stopper portions 30A3, 30A4. At this time, the movable arms 22Aa, 22Ab cannot be open again such that the clip 20A is locked to the pressing tube 30A.

As shown in FIG. 14, the applicator 50A includes an insertion portion 51A, an operation portion 60A, and operation wires 62Aa, 62Ab. The insertion portion 51A is an elongated member inserted into the body, wherein the proximal end thereof is connected to the operation portion 60A, and the distal end thereof is detachably connected to the pressing tube 30A. The main body portion of the operation portion 60A are divided into two portions and two sliders 61Aa, 61Ab are provided in the two portions respectively. Proximal ends of operation wires 62Aa, 62Ab are connected to the sliders 61Aa, 61Ab, respectively. The operation wires 62Aa, 62Ab are inserted through the inner cavity of the insertion portion 51A, and distal ends thereof are connected to the first connection member 40Aa and the second connection member 40Ab, respectively.

The first connection member 40Aa and the second connection member 40Ab are elongated members inserting through the pressing tube 30A. The proximal end of the first connection member 40Aa is connected to the distal end of the operation wire 62Aa. A first hook claw 40Aa1 is provided at the distal end of the first connection member 40Aa. The first hook claw 40Aa1 engages with the second pin 24A1 inserted into the first sliding groove 22Aa1 of the movable arm 22Aa. The proximal end of the second connection member 40Ab is connected to the distal end of the operation wire 62Ab. A second hook claw 40Ab1 is provided at the distal end of the second connection member 40Ab. The second hook claw 40Ab1 engages with the fourth pin 24A2 inserted into the second sliding groove 22Ab1 of the movable arm 22Ab. Each of the first hook claw 40Aa1 and the second hook claw 40Ab1 is formed in a C-shape.

Hereinafter, the movable arm 22Aa will be taken as an example to describe the grasping operation, the locking operation, and the engagement releasing operation of the movable arm. The operations of the movable arm 22Ab is the same with that of the movable arm 22Aa.

Figure 18A:
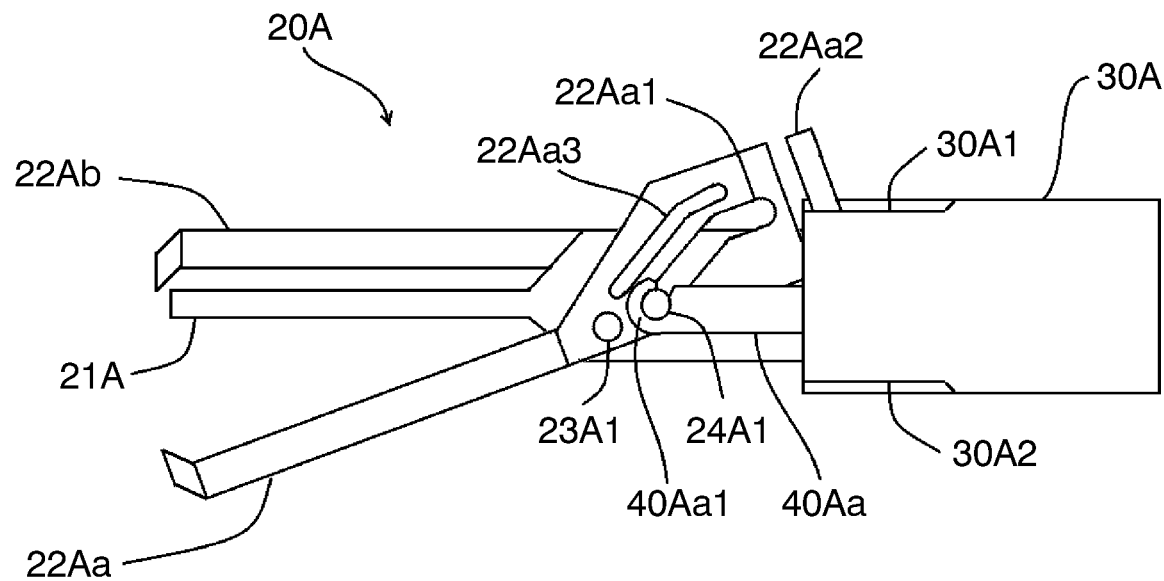
FIG. 18A to FIG. 18E are schematic views showing the grasping operation, the locking operation, and the engagement releasing operation of the clip device according to the second embodiment.

As shown in FIG. 18A, when the movable arm 22Aa is open with respect to the fixed arm 21A, the second pin 24A1 is positioned at the distal end of the first sliding groove 22Aa1. After placing the target tissues between the movable arm 22Aa and the fixed arm 21A, when the slider 62Aa is moved toward the proximal end side in the operation portion 60A, the operation wire 62Aa is pulled toward the proximal end side and the second pin 24A1 is moved toward the proximal end side in the first sliding groove 22Aa1. Accordingly, the movable arm 22Aa is rotated toward the fixed arm 21A side (that is, the closing direction).

Figure 18B:
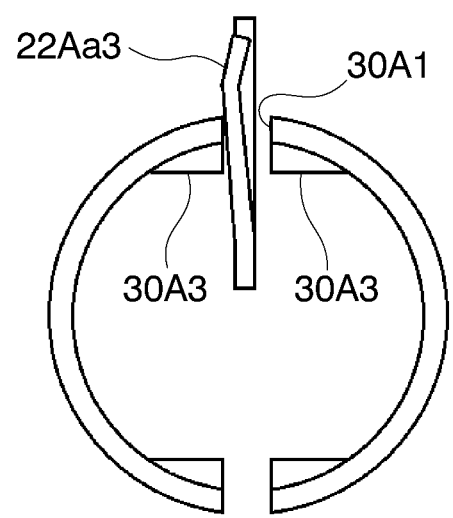

As the second pin 24A1 slides toward the proximal end side of the first sliding groove 22Aa1, the proximal end portion of the movable arm 22Aa moves into the inner cavity of the pressing tube 30A through the groove portion 30A1. At this time, as shown in FIG. 18B, the protrusion portion 22Aa2 is pressed by the edge portion of the groove portion 30A1 such that the protrusion portion 22Aa2 is elastically deformed to the fixed arm side (the right side in FIG. 18B).

Figure 18C:
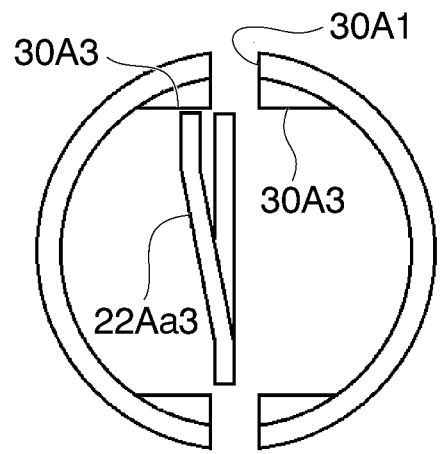
Figure 18D:
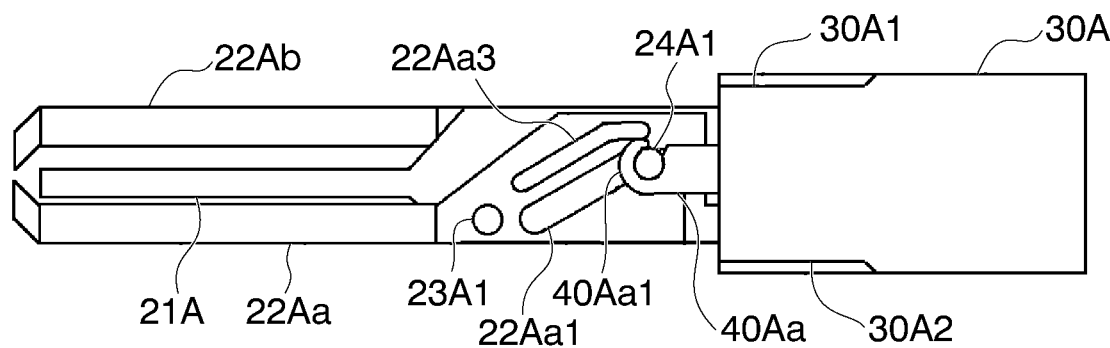

When the protrusion portion 22Aa2 completely enters the inner cavity of the pressing tube 30A, the protrusion portion 22Aa2 is not pressed by the edge portion of the groove portion 30A1 so as to restore to the slanted state in the direction away from the fixed arm side (the left side in FIG. 18C). At this time, as shown in FIG. 18C, the end of the protrusion portion 22Aa2 comes into contact with the stopper portion 30A3 of the pressing tube 30A and it is impossible to come out from the groove portion 30A1 again. Accordingly, as shown in FIG. 18D, the movable arm 22Aa is locked to be impossible to open again.

Figure 18E:
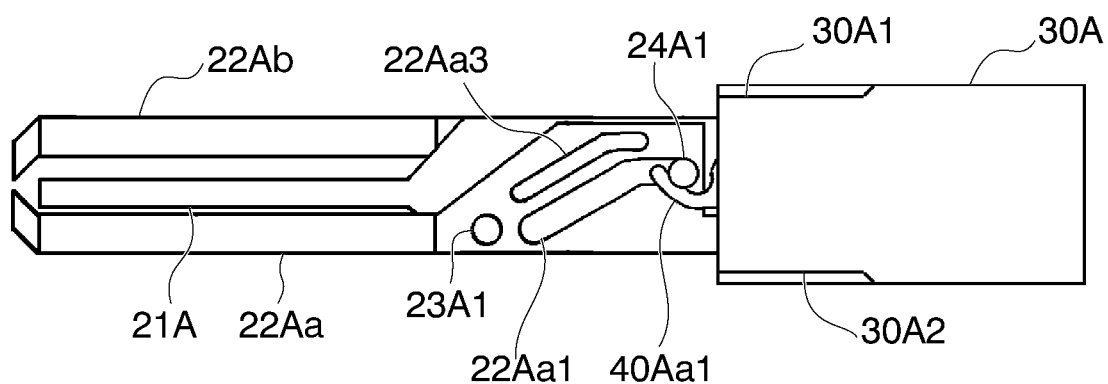

After the movable arm 22Aa is locked, when the operation wire 62Aa is further pulled toward the proximal end side, the second pin 24A1 moves toward the proximal end of the first sliding groove 22Aa1. The second pin 24A1 reaching the proximal end of the first sliding groove 22Aa1 does not further move to the proximal end side such that the reaction force from the second pin 24A1 and received by the first hook claw 40Aa1 increases. As shown in FIG. 18E, when the reaction force from the second pin 24A1 and received by the first hook claw 40Aa1 exceeds the predetermined threshold value, the first hook claw 40Aa1 deforms and the engagement of the first hook claw 40Aa1 and the second pin 24A1 is released.

During the process of actually using the clip device, due to the manufacturing variations, there is also variations in the strength of the first hook claw 40Aa1 and the second hook claw 40Ab1. Accordingly, there is a situation in which the hook claw firstly deforms before the movable arm is locked and the engagement of the connection member and the arm is unintentionally released. In order to prevent such a situation, contact portions described below are provided in the two movable arms. The structure of the contact portions provided in the two movable arms are the same, and the movable arm 22Aa will be taken as an example for description.

As shown in FIG. 14, FIG. 15, and FIG. 18A, the contact portion 22Aa3 is formed on the side surface of the movable arm 22Aa. The contact portion 22Aa3 is formed along the first sliding groove 22Aa1 and at a certain distance from the first sliding groove 22Aa1. During the process when the second pin 24A1 slides along the first sliding groove 22Aa1, part of the first hook claw 40Aa1 positions between the contact portion 22Aa3 and the second pin 24A1, and the contact portion 22Aa3 is in contact with the first hook claw 40Aa1 in the direction orthogonal to the axial direction of the second pin 24A1. Accordingly, it is possible to prevent the first hook claw 40Aa1 from receiving the reaction force from the second pin 24A1 to be deformed.

Figure 19:
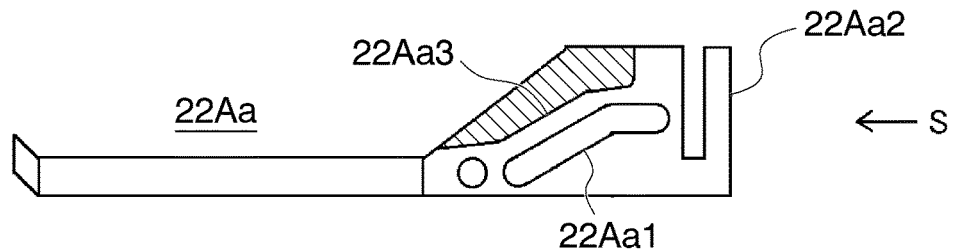
FIG. 19 is a schematic view showing a modification of a contact portion.

As shown in FIG. 15a, the contact portion 22Aa3 is an elongated convex portion formed to protrude from the side surface of the movable arm 22Aa. Otherwise, as shown in FIG. 19, the contact portion 22Aa3 may be a step portion formed by a partial region (the shadow region) on the side surface of the movable arm 22Aa further raising from the sliding passage region of the first hook claw 40Aa1.

As shown in FIG. 18D, in the longitudinal direction of the movable arm 22Aa, the most proximal end of the contact portion 22Aa3 is formed at the position where the second pin 24A1 is located when the movable arm 22Aa is locked. After the movable arm 22Aa is locked, during the process when the second pin 24A1 continues to move to the proximal end side of the first sliding groove 22Aa1 and at the time when the second pin 24A1 is positioned at the proximal end of the first sliding groove 22Aa1, the first hook claw 40Aa1 is not in contact with the contact portion 22Aa3 anymore. Accordingly, as shown in FIG. 18E, after the movable arm 22A is locked, it is permitted that the first hook claw 40Aa1 is deformed and the engagement with the second pin 24A1 is released.

Third Embodiment

Compared with the second embodiment, the structure of the first engaging portion and the second engaging portion according to the third embodiment are different. Other structure thereof is the same with that of the second embodiment.

Figure 20:
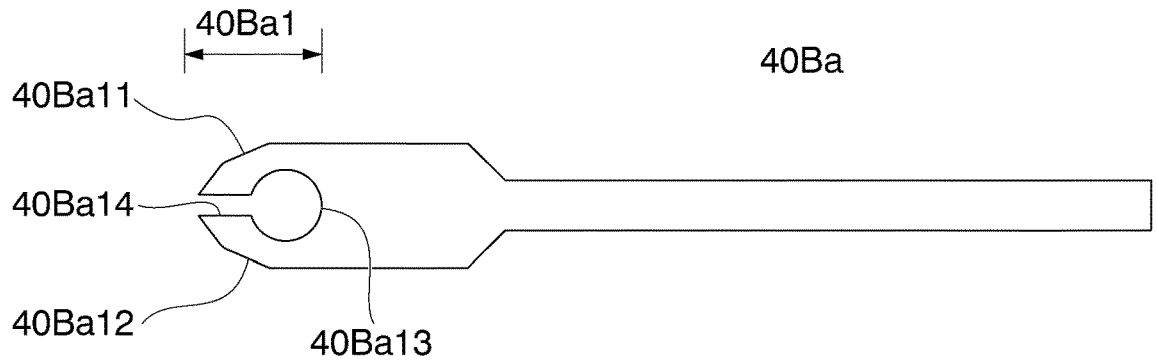
FIG. 20 is a side view showing a first connection member according to a third embodiment.

FIG. 20 is a side view showing a first connection member 40Ba according to the third embodiment. The first engaging portion 40Ba1 formed from a first engaging claw 40Ba11 and a second engaging claw 40Ba12 is provided at the distal end of the first connection member 40Ba.

The first engaging claw 40Ba11 and the second engaging claw 40Ba12 are provided to be opposite to each other. An accommodation hole 40Ba13 and a notch 40Ba13 are formed between the first engaging claw 40Ba11 and the second engaging claw 40Ba12.

When the first engaging portion 40Ba1 and the second pin 24B1 are engaged with each other, the accommodation hole 40Ba 13 is configured to accommodate the second pin 24B1.

The distance between the first engaging claw 40Ba11 and the second engaging claw 40Ba12 in the notch 40Ba14 is larger than the outer diameter of the second pin 24B1. The first engaging claw 40Ba11 and the second engaging claw 40Ba12 have a certain elasticity and can be expanded with respect to each other. Accordingly, the second pin 24B1 can be pressed into the accommodation hole 40Ba13 via the notch 40Ba14 to make the first engaging portion 40Ba1 and the second pin 24B1 to be engaged with each other. On the other side, the second pin 24B1 in the accommodation hole 40Ba13 can be disengaged from the first engaging portion 40Ba1 via the notch 40Ba14 to disengage the engagement between the first engaging portion 40Ba1 and the second pin 24B1.

The structure of the second connection member is the same with that of the first connection member 40Ba, and the duplicate description will be omitted.

During the process of actually using the clip device, due to the manufacturing variations, there is also variations in the strength of the engaging claws. Accordingly, there is a situation in which the engaging claw firstly deforms before the movable arm is locked and the engagement is unintentionally released. In order to prevent such a situation, contact portions described below are provided in the two movable arms. The structure of the contact portions provided in the two movable arms are the same, and the movable arm 22Ba will be taken as an example for description.

Figure 21:
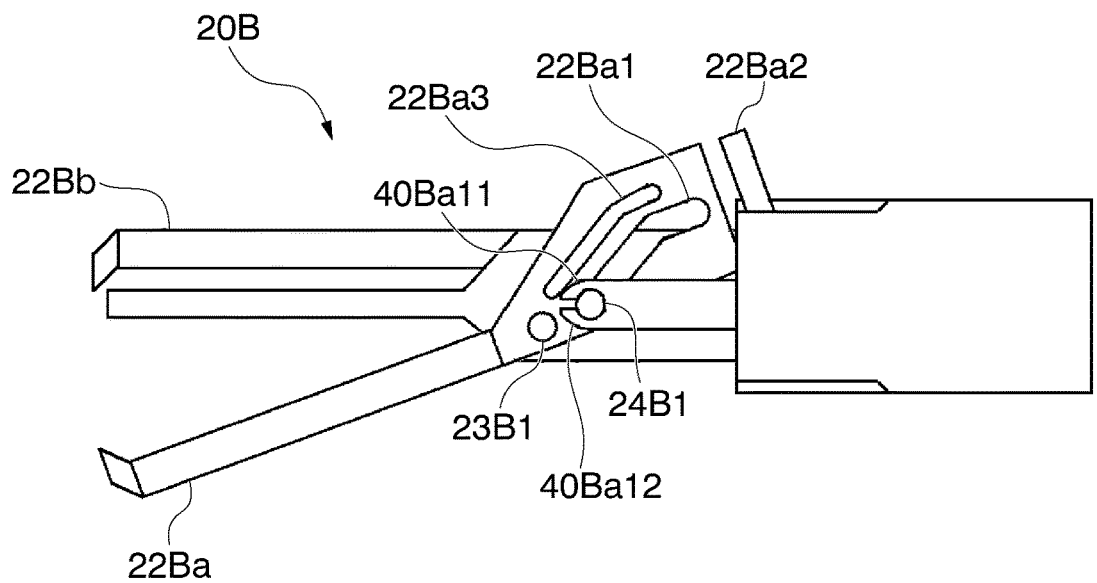
FIG. 21 to FIG. 23 are schematic views showing the grasping operation, the locking operation, and the engagement releasing operation of the clip device according to the third embodiment.

As shown in FIG. 21, the contact portion 22Ba3 is formed on the side surface of the movable arm 22Ba. The contact portion 22Ba3 is formed along the first sliding groove 22Ba1 and at a certain distance from the first sliding groove 22Ba1. During the process when the second pin 24B1 slides along the first sliding groove 22Ba1, part of the first engaging claw 49Ba11 positions between the contact portion 22Ba3 and the second pin 24B1, and the contact portion 22Ba3 is in contact with the first engaging claw 40Ba11 in the direction orthogonal to the axial direction of the second pin 24B1. Accordingly, it is possible to prevent the first engaging claw 40Ba1 from receiving the reaction force from the second pin 24B1 to be deformed.

Similar to the second embodiment, the contact portion 22Ba3 may be the elongated convex portion formed to protrude from the side surface of the movable arm 22Ba, or may be the step portion formed by a partial region on the side surface of the movable arm 22Ba further raising from the sliding passage region of the first engaging claw 40Ba11.

Figure 22:
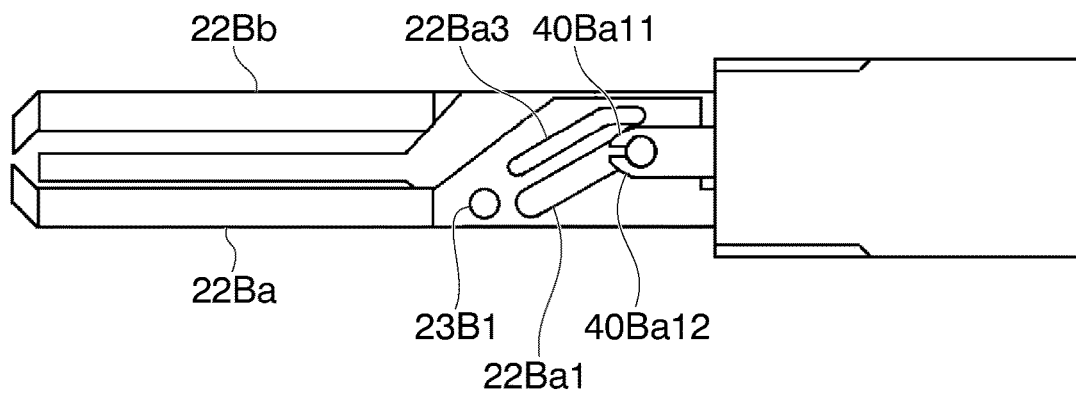

In the longitudinal direction of the movable arm 22Ba, the most proximal end of the contact portion 22Ba3 is formed at the position where the second pin 24B1 is located when the movable arm 22Ba is locked. Accordingly, as shown in FIG. 22, when the movable arm 22Ba is locked, the second pin 24B1 can come into contact with the contact portion 22Ba3 again.

Figure 23:
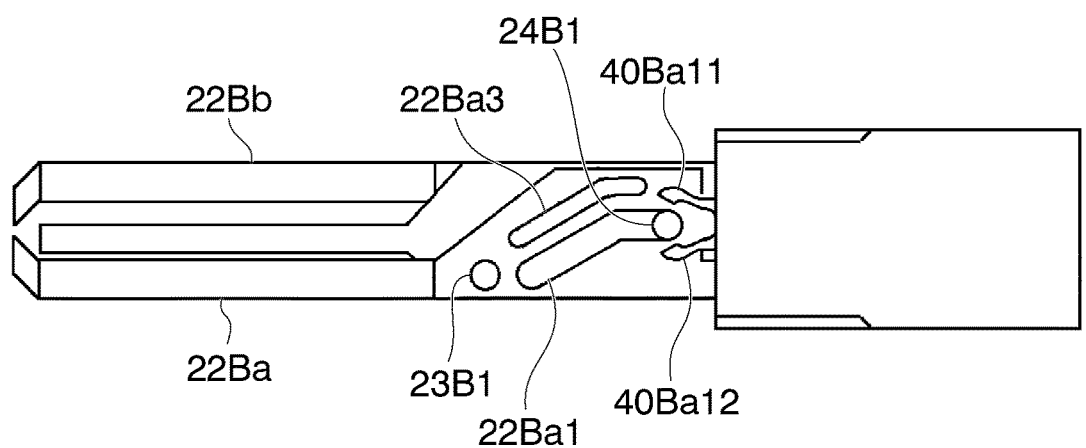

After the arm 22Ba is locked, when the second pin 24A1 is positioned at the proximal end of the first sliding groove 22Ba1, the first engaging claw 40Aa11 is not in contact with the contact portion 22Ba3. Accordingly, as shown in FIG. 23, after the movable arm 22Ba is locked, it is permitted that the first engaging claw 40Aa11 is deformed and the engagement with the second pin 24B1 is released.

Figure 24:
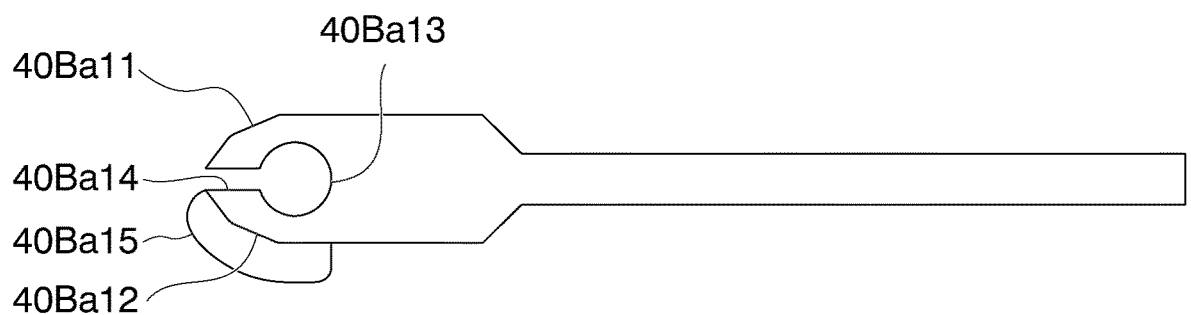
FIG. 24 is a schematic view showing a modification example of a connection member according to the third embodiment.

As shown in FIG. 24, it is preferable that the width of the second engaging claw 40Ba12 is larger than that of the first engaging claw 40Ba11 by providing a reinforcing portion 40Ba15. The second engaging claw 40Ba12 is not in contact with the contact portion 22Ba3 such that it is possible that the second engaging claw 40Ba12 is deformed before the movable arm 22Ba is locked and the engagement with the second pin 24B1 is released. It is possible to prevent the second engaging claw 40Ba12 that is not in contact with the contact portion 22Ba3 from being deformed before the movable arm 22Ba is locked by increasing the width of the second engaging claw 40Ba12. Otherwise, the thickness of the second engaging claw 40Ba12 may be larger than that of the first engaging claw 40Ba11.

Fourth Embodiment

A fourth embodiment of the present disclosure will be described referring to FIG. 25 to FIG. 31. In the following description, the common configurations that have been described will be designated to the same reference signs and the duplicate description will be omitted.

Figure 25:
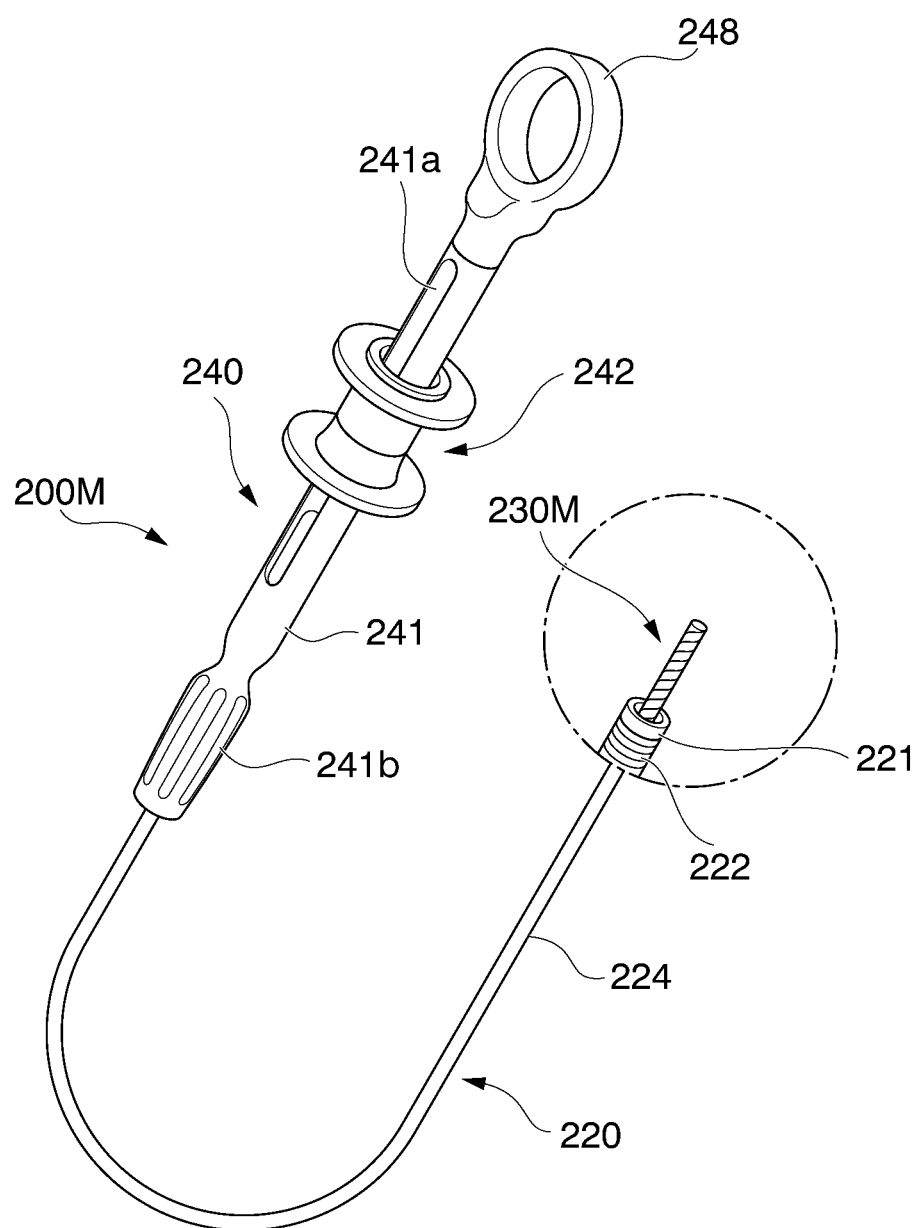
FIG. 25 is a view showing a clip introducing device of a clip device according to a fourth embodiment.

FIG. 25 is a view showing a clip introduction device of a clip device according to the present embodiment. A clip device 100M according to the present embodiment includes a clip unit (endoscopic treatment device) 1M and a clip introduction device 200M for operating the clip unit 1M. The clip unit 1M is used by being loaded in the clip introduction device 200M.

The clip introduction device 200M includes a sheath 200, an operation wire 230M, and an operation portion 240. For example, the clip introduction device 200M is inserted through the treatment device insertion channel of the endoscope and is combined with the endoscope to be used. Accordingly, the sheath 220 is formed to be enough long compared with the length of the treatment device insertion channel of the endoscope. The sheath 220 has the flexibility and is bent following the bending of the insertion portion of the endoscope.

The sheath 220 includes a distal end tip 221, a distal side coil 222, and a hand-side coil 224, and the whole heath 220 is formed in an elongated tubular shape. The distal side coil 222 is disposed at the distal end side of the sheath 220. The distal end tip 221 is disposed at the distal end portion of the distal side coil 222.

Figure 26:
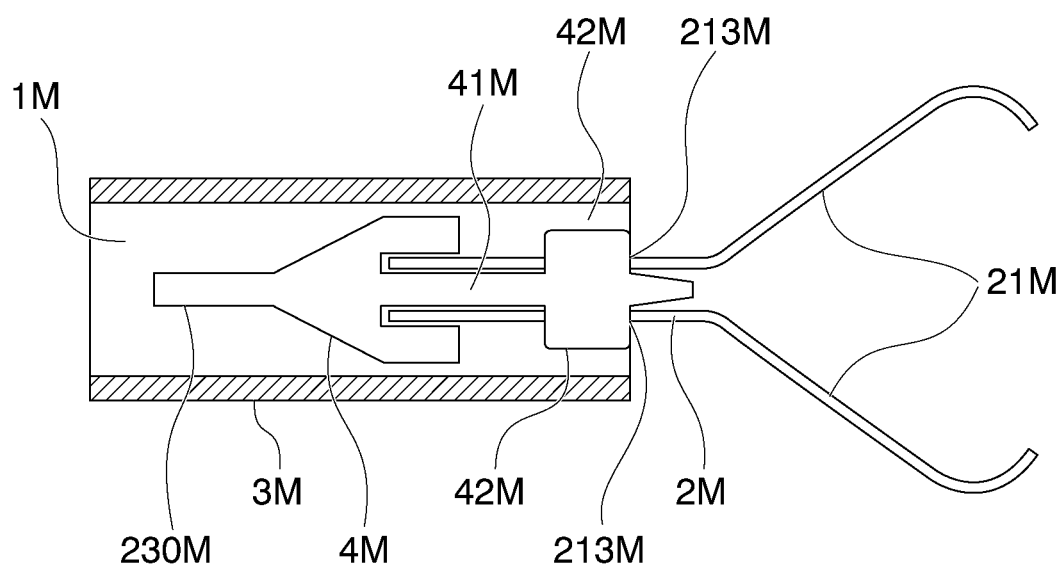
FIG. 26 is a view showing a schematic configuration of a clip unit according to the fourth embodiment.

FIG. 26 is a view showing the schematic configuration of the clip unit 1M according to the present embodiment. The clip unit (endoscopic treatment device) 1M includes a clip 2M having a pair of arms 21M being openable and closable, a pressing tube 3M having a substantially tubular shape, and a connection member 4M configured to connect the pair of arms 21M and the operation wire 230M. As shown in FIG. 25 and FIG. 26, the operation wire 230M is configured to operate the connection member 4M, and the proximal end thereof is connected to the operation portion 240 of the clip introduction device 200M, and the distal end thereof is connected to the connection member 4M.

Figure 27:
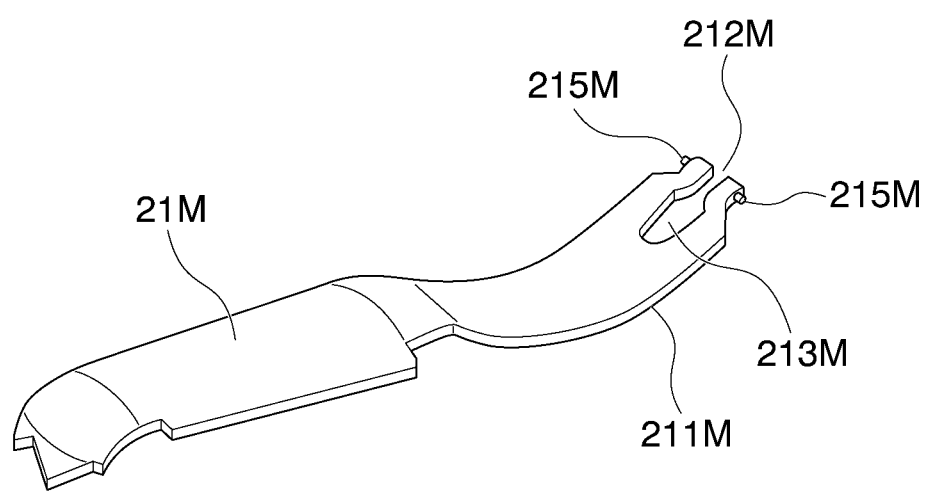
FIG. 27 is a perspective view showing a configuration of an arm of the clip unit.

FIG. 27 is a perspective view showing the configuration of the arms of the clip unit 1M. A tail 211M of the arms 21M (that is, the proximal end side of the arms 21M) includes a snap-fit hole 213M, and the distal end of the connection member 4M is engaged with the snap-fit hole 213M. The tail 211M of the arms 21M includes a slit 212M communicating with the snap-fit hole 213M, and the proximal end of the slit 212M opens at the proximal end of the tail of the arms 21M. The tail 211M of the arms 21M is elastically deformable, and when the connection member 4M attempts to pass through the slit 212M from the snap-fit hole 213M, the tail 211M of the arms 21M is elastically deformed and the width of the slit 212M is expanded such that the distal end of the engaged connection member 4M is separated from the arms 21M through the slit 212M.

Of course, the shape and the configuration of the snap-fit hole 213M is not limited to the above-described shape and configuration and may be other shape and configuration that is detachably engaged with the distal end of the connection member 4M.

As shown in FIG. 26, the connection member 4M is configured to engage with the pair of arms 21M and to be advanceable and retractable inside the pressing tube 3M, and the connection member 4M forms an arrowhead portion 41M extending at the distal end of the connection member 4M. A pair of snap-fit protrusion portions 42M are formed to protrude in the radial direction from the distal end thereof in the arrowhead portion 41M. The snap-fit protrusion portions 42M are engaged with the snap-fit hole 213M by being fit in the radial direction of the pressing tube 3M such that the arms 21M and the connection member 4M are movably connected. The snap-fit protrusion portions 42 and the snap-fit hole 213M do not necessarily have to be paired, and may be at least one.

Figure 28:
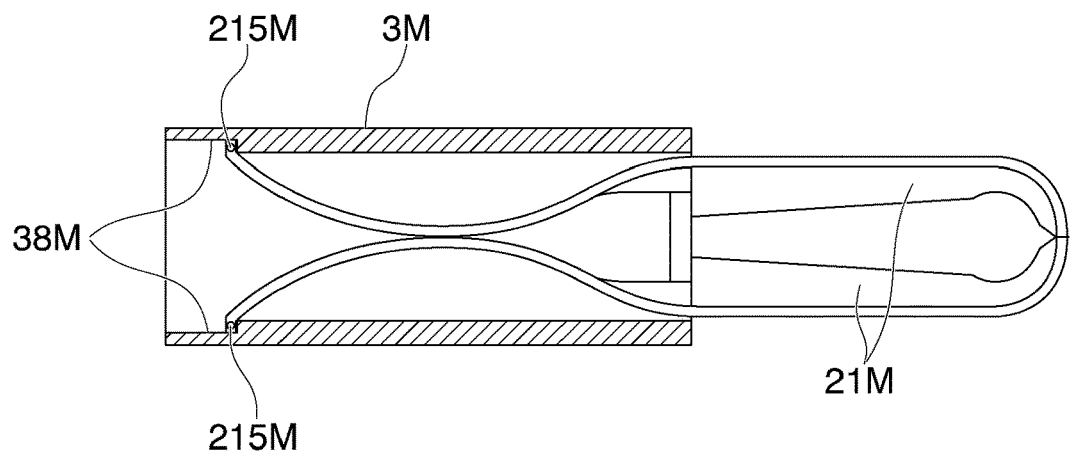
FIG. 28 is a view showing a state in which a tail of the arm of the clip unit is engaged with the pressing tube.

Furthermore, as shown in FIG. 27, in the tail 211M of the arms 21M, an arm-tail convex portion 215M is further formed to protrude toward the direction intersecting with the thickness direction of the arms 21M. FIG. 28 is a view showing the situation in which the tail of the arms of the clip unit is engaged with the pressing tube. As shown in FIG. 28, when the arm-tail convex portion 215M is positioned inside the pressing tube 3M, the protrusion direction of the arm-tail convex portion 215M extends to intersect with the longitudinal direction of the pressing tube 3M.

As shown in FIG. 28, a step portion 38M is formed on the inner wall of the pressing tube 3M biasing to the proximal end side of the pressing tube 3M, and when the pair of arms 21M is closed, the arm-tail convex portion 215M and the step portion 38M are engaged with each other such that the arms 21M are locked to the pressing tube 3M.

According to the clip unit 1M of the present embodiment, the operation portion 240 is operated to pull the operation wire 230 and move the connection member 4M to the proximal end side such that the pair of arms 21M are retracted in the pressing tube 3M and the pair of arms 21M enters the closed state. In the closed state, the arm-tail convex portion 215M of the arms 21m are engaged with the step portion 30M of the pressing tube 3M such that the movement of the arms 21M inside the pressing tube 3M is restricted. When the operation wire 230 is further pulled, the tail 211M of the arms 21M receives the force due to the snap-fit protrusion portion 42M provided in the connection member 4M to be elastically deformed and the width of the slit 212M is expanded, and the snap-fit protrusion portion 42M is separated from the snap-fit hole 213M. The arm-tail convex portion 215M is engaged with the step portion 38M of the pressing tube 3M so as to realize the locking and the releasing of the clip 2M.

Figure 29:
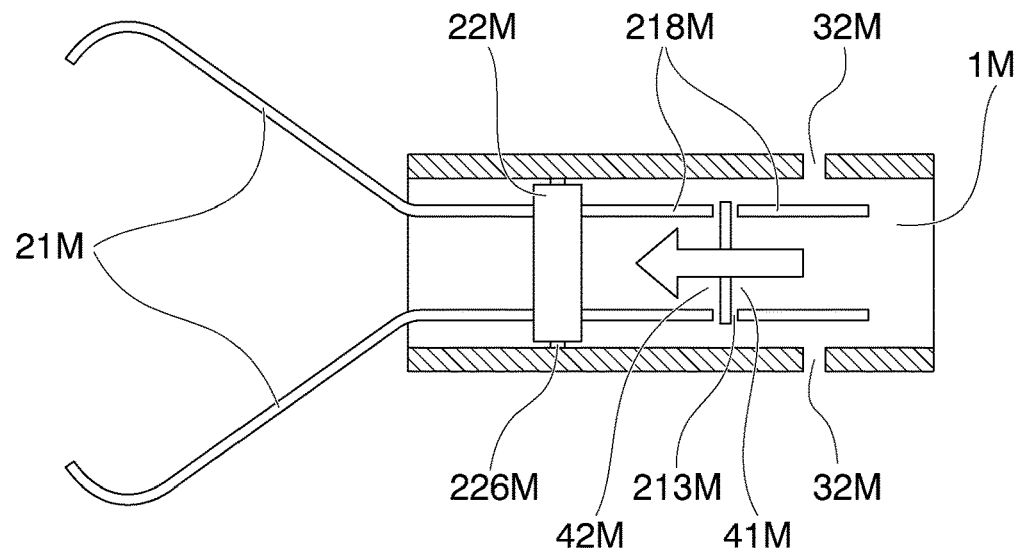
FIG. 29 is a view showing a schematic configuration of the other clip unit as a modification example according to the fourth embodiment.

FIG. 29 is a view showing the schematic configuration of another clip unit 1M according to the fourth embodiment as a modification example. As shown in FIG. 29, the distal end of the connection member 4M has the arrowhead portion 41M, and the pair of snap-fit protrusion portions 42M (in FIG. 29, only one side thereof is designated with the reference sign, and the reference sign to the other side is omitted) are formed to protrude in the radial direction from the arrowhead portion 41M. The pair of arms 21M are joined and fixed at the arm fixation portion 22M. Furthermore, each of the pair of arms 21M extends toward the proximal end side from the arm fixation portion 22M to form an arm extension portion 218M (in FIG. 29, only one side thereof is designated with the reference sign, and the reference sign to the other side is omitted). The snap-fit hole 213M (in FIG. 29, only one side thereof is designated with the reference sign, and the reference sign to the other side is omitted) is provided in the tail of the arm extension portion 218M, and the snap-fit protrusion portion 42M and the snap-fit hole 213M are engageable with each other due to the advancement and the retraction of the connection member 4M. The shape and the configuration of the present snap-fit hole 213M may be set to be the same with that of the above-described embodiment. In the arm fixation portion 22M, an elastic protrusion portion 226M is provided in the direction orthogonal to the longitudinal direction of the pressing tube 3M, that is, in the direction from the arm fixation portion 22M toward the inner circumferential surface of the pressing tube 3M. A step portion 32M is provided in the inner wall of the pressing tube 3M biasing to the proximal end of the pressing tube 3M, and the step portion 32M is configured to lock the advancement and the retraction of the arms 21M inside the pressing tube 3M by engaging with the elastic protrusion portion 226M. Although at least one elastic protrusion 226M may be provided, it is preferable to provide the pair of elastic protrusions 226M at positions being opposite to each other in the radial direction in order to securely lock the pair of arms 21M in the holding tube 3M.

In FIG. 29, the step portion 32M is the hole penetrating the inner wall and the outer wall of the pressing tube 3M; however, the step portion 32M is not limited to the hole and may be the concave portion formed on the inner wall of the pressing tube 3M without penetrating to the outer wall of the pressing tube 32M. Similarly, the step portion 32M may be the convex portion formed in the inner wall of the pressing tube 3M. Furthermore, as shown in FIG. 30, the step portion 32M may be a ring formed of the metal material disposed inside the pressing tube 3M.

Figure 30:
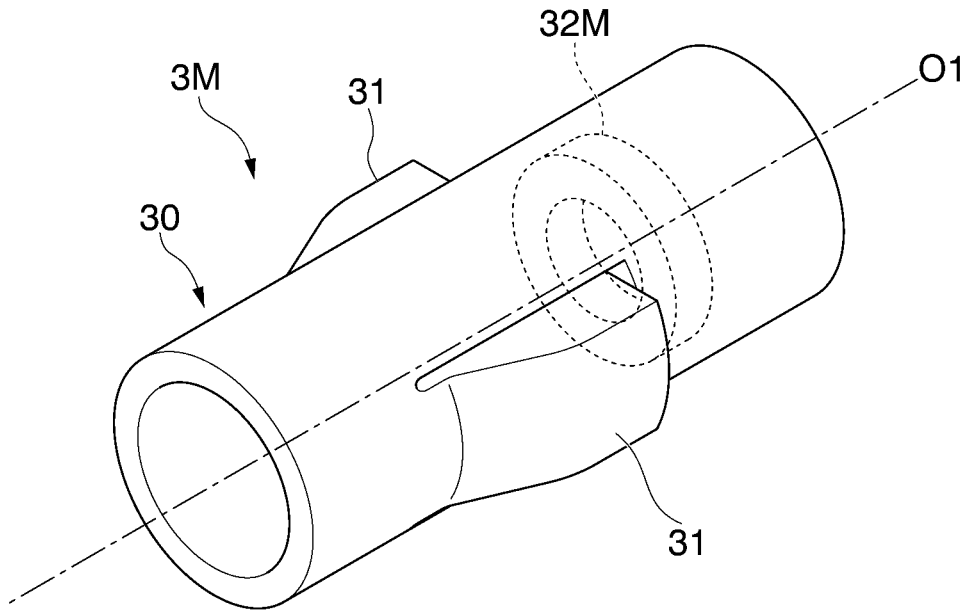
FIG. 30 is a perspective view showing the pressing tube of the other clip unit according to the fourth embodiment.
Figure 31:
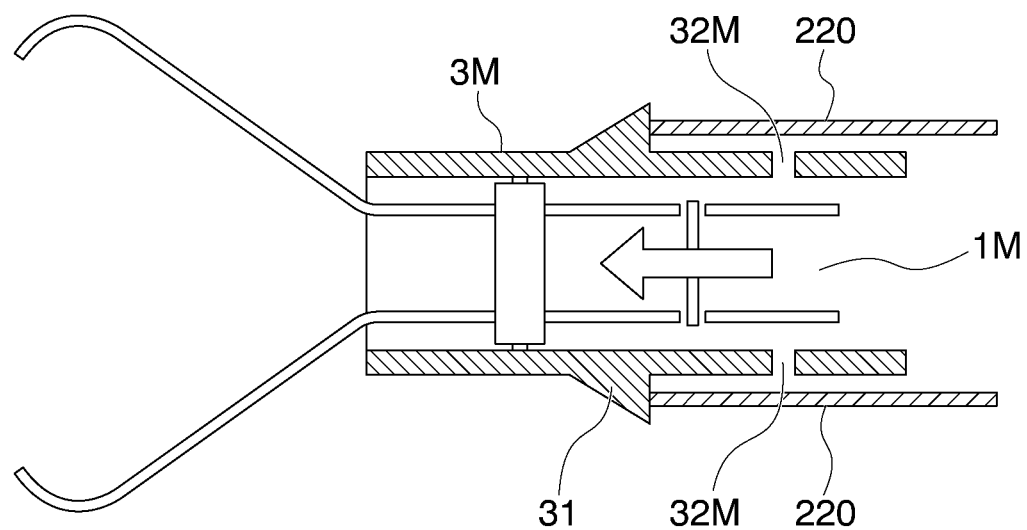
FIG. 31 is a view showing the clip unit including the pressing tube shown in FIG. 30.

FIG. 30 is a perspective view showing the pressing tube 3M of another clip unit 1M according to the present embodiment. FIG. 31 is a view showing the clip unit 1M having the pressing tube 3M as shown in FIG. 30. The pressing tube 3M includes a pressing tube main body 30 formed in the tubular shape, an elastically deformable protrusion-depression wing 31 extending outwardly in the radial direction, and the step portion 32M. The pressing tube main body 30 is formed by the injection molding using a material more flexible than that of the clip unit 1M, for example, the thermoplastic resin having appropriate elasticity such as the PPA (polyphthalamide), the PA (polyamide), the PEEK (polyetheretherketone), the LCP (liquid crystal polymer) and the like. The pressing tube main body 30 may be formed of the metal material instead of the thermoplastic resin.

Furthermore, as shown in FIG. 30, the wing 31 is a pair of convex portions protruding from and depressing with respect to the outer circumferential surface of the pressing tube 3M, and the above-described ring made of the metal material as the step portion 32M is provided at the proximal end side of the protrusion-depression wing 31.

According to the fourth embodiment of the present disclosure, the tails of the arms are directly connected with the clip introduction device and the internal space of the clip unit may be maximally utilized.

Fifth Embodiment

Figure 32:
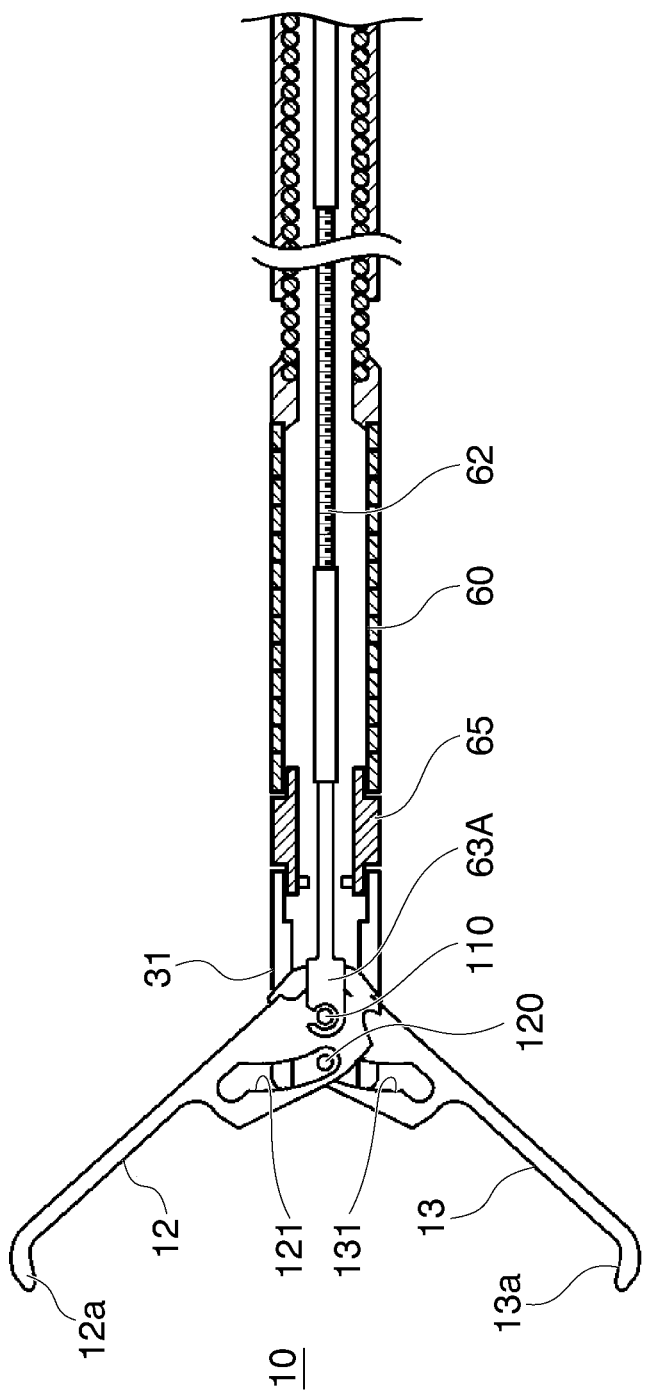
FIG. 32 is a cross-sectional view showing the vicinity of the clip unit in the clip device according to the fourth embodiment.

In FIG. 32, the clip unit includes the clip 10 and the pressing tube 31. The pressing tube 31 is configured to at least accommodate the proximal end portion of the clip 10. The proximal end of the pressing tube 31 is connected to the distal end of an insertion member 60 via the connection member 65. The operation wire 62 is inserted through the inside passage of the insertion member 60. The connection member 63A is configured to connect the distal end of the operation wire 62 and the proximal end portion of the clip 10.

As shown in FIG. 32, the clip 10 according to the present embodiment includes two of arms 12, 13. The arms 12, 13 includes a first pin (intermediate member) 110 in the proximal end portion thereof, and the first pin 110 is configured to movably connect the two arms 12, 13. The two arms 12, 13 further includes long grooves 121, 131 respectively for the second pin 120 to be inserted through. The second pin 120 inserted into the long grooves 121, 131 may be slided along the long grooves 121, 131. The two ends of the second pin 120 are fixed to the pressing tube 31. When the first pin 110 is moved forwardly and backwardly via the operation wire 62, the second pin 120 slides along the long grooves 121, 131 and the two arms 12, 13 open and close such that the distal ends 12a, 13a grasp or release the target issues.

Figure 33:
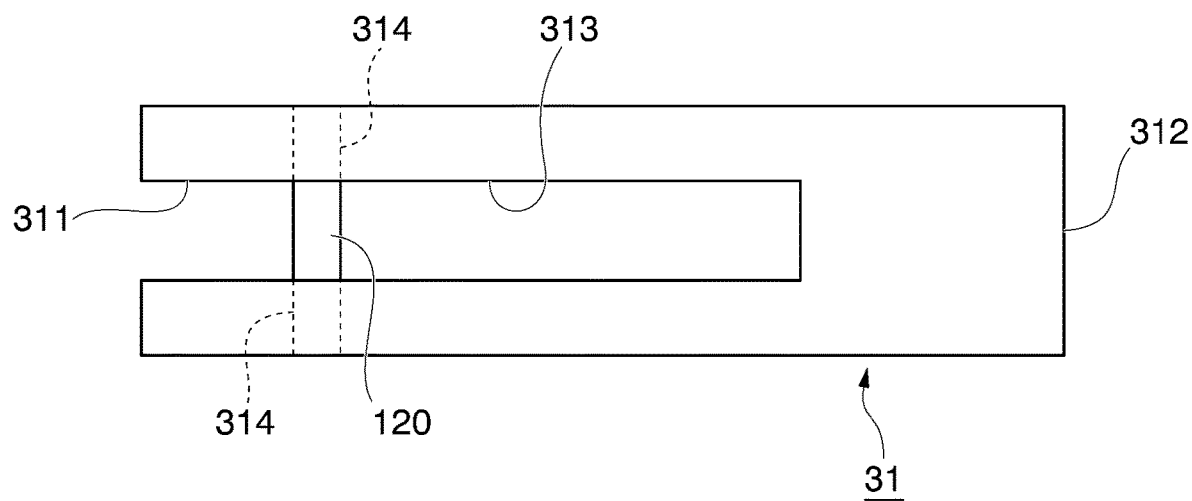
FIG. 33 is a schematic view showing the pressing tube in the clip device according to the fourth embodiment.

As shown in FIG. 32 and FIG. 33, the pressing tube 31 is formed in a hollow tubular shape, and the pressing tube 31 has a distal-end opening 311 and a proximal-end opening 312. Two tube wall grooves 313 being opposite to each other are provided on the tube wall of the pressing tube 31, and when the two arms 12, 13 are opened, the two arms 12, 13 pass through the tube wall grooves 313. In the pressing tube 31, a pair of pin holes 313 to which the two ends of the second pin 120 are fixed are provided on the tube wall thereof.

Figure 34:
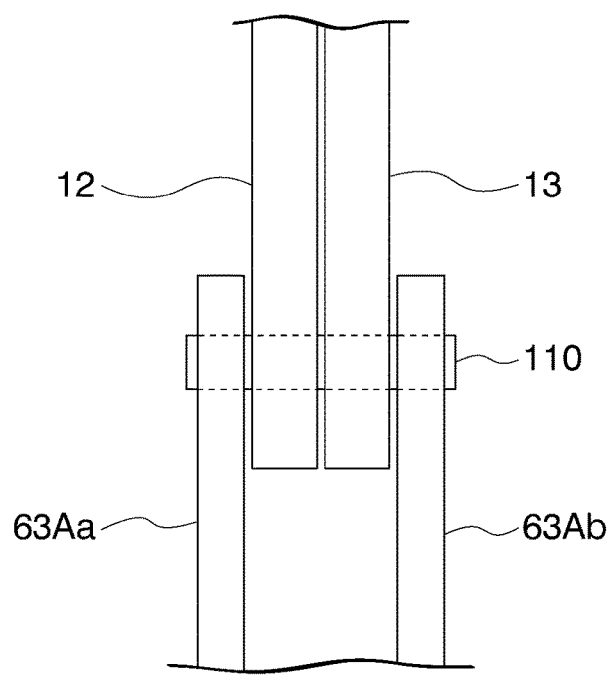
FIG. 34 is a schematic view showing the connection relationship of the connection member and the arm in the clip device according to the fourth embodiment.

As shown in FIG. 32 and FIG. 34, the connection member 63A according to the present embodiment includes a first connection member 63Aa and a second connection member 63Ab. The first connection member 63Aa and the second connection member 63Ab are connected to the two ends of the first pin 110 and come into contact with the two arms 12, 13 from the two sides, respectively. The first connection member 63Aa and the second connection member 63Ab may have the same shape and dimension.

Figure 35:
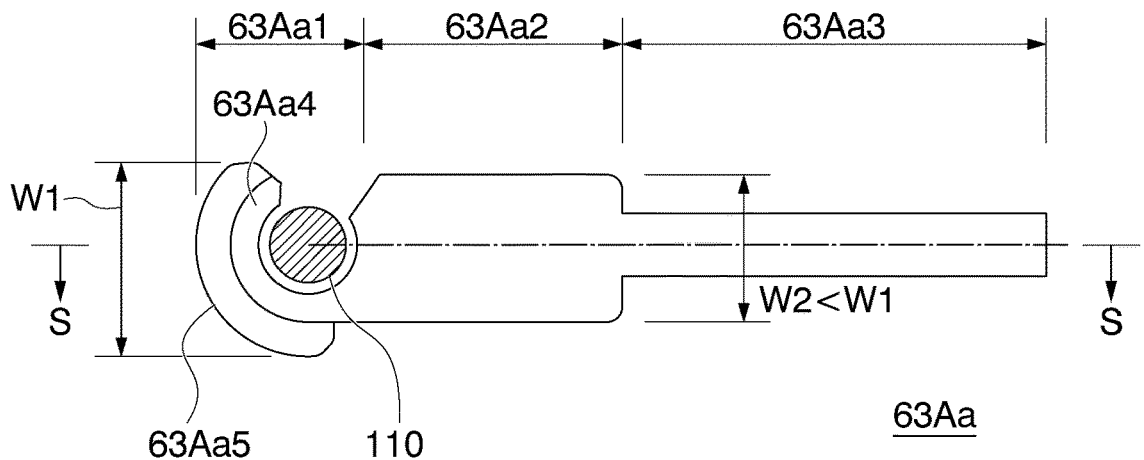
FIG. 35 is a side view showing the connection member in the clip device according to the fourth embodiment.

FIG. 35 is a side view of the first connection member 63Aa. The first connection member 63Aa is integrally formed of an elongated metal plate material. As shown in FIG. 35, the first connection member 63Aa includes a distal end portion 63Aa1, a main body portion 63Aa2, and a proximal end portion 63Aa3 from the distal end side.

The proximal end portion 63Aa3 of the first connection member 63Aa is connected to the distal end of the operation wire 62. The width of the proximal end portion 63Aa3 is smaller than the width of the distal end portion 63Aa1 and the main body portion 63Aa2.

The distal end portion 63Aa1 of the first connection member 63Aa is the first hook claw (engaging portion). Similarly, the distal end portion of the second connection member 63Ab is the second hook claw (engaging portion). The first hook claw 63Aa4 and the second hook claw are formed in the C-shape and form the internal space for hooking the end portion of the first pin 110, respectively. In other words, the first hook claw 63Aa4 and the second hook claw are configured to hook the two ends of the first pin 110. At the time of separating the clip 10 and the connection member 63A, the operation wire 62 is pulled toward the proximal end side such that the first hook claw 63Aa4 and the second hook claw receive the force to be deformed and the connection with the first pin 110 is released.

The two arms 12, 13 are interposed between the first hook claw 63Aa4 and the second hook claw. It is preferable that the first hook claw 63Aa4 and the second hook claw come into contact with the arms 12, 13 from the two sides so as to prevent the arms 12, 13 from moving in the axial direction of the first pin 110.

As shown in FIG. 35, the contact portion 63Aa5 extends from the first hook claw 63Aa4 so as to increase the contact area with the arms. The contact portion 63Aa5 may be integrally formed with the first hook claw 63Aa4, or the first hook claw 63Aa4 and the contact portion 63Aa5 may be formed individually and then joined together.

It is preferable that the width of the hook claw where the contact portion is formed is larger than the width of other portion of the connection member. For example, as shown in FIG. 35, the width W1 of the first hook claw 63Aa4 where the contact portion 63Aa5 is larger than the width W2 of the main body portion 63Aa2.

Figure 36:
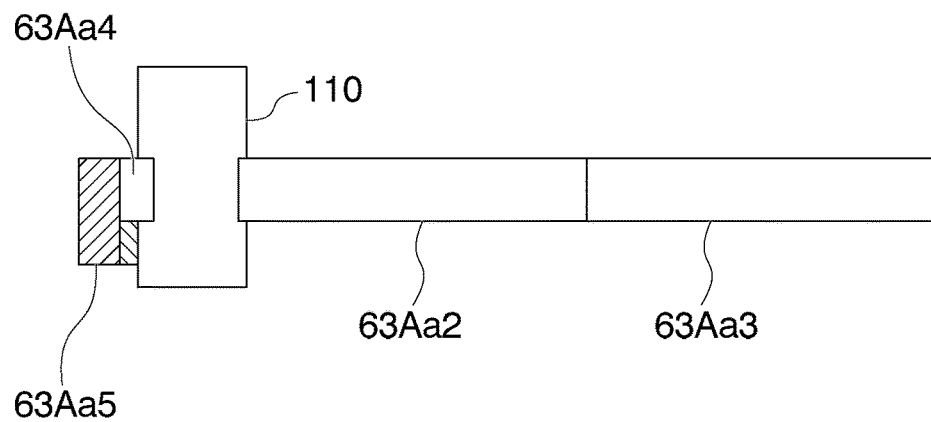
FIG. 36 is a top view showing a modification example in which the thickness of the contact portion is larger than the thickness of the hook claw that is viewed from the direction S shown in FIG. 35.

The thickness of the contact portion 63Aa5 is the same with the thickness of the first hook claw 63Aa4. Instead, as shown in FIG. 36, the thickness of the contact portion 63Aa5 may be larger than the thickness of the first hook claw 63Aa4. In the connection member, the thickness of the first hook claw 63Aa4 where the contact portion 63Aa5 is formed may be larger than the thickness of other portions of the connection member, for example, may be larger than the thickness of the main body portion 63Aa2. In the case in which the thickness of the first hook claw 63Aa4 is larger than the thickness of the main body portion 63Aa2, and it is possible to maintain enough strength of the first hook claw 63Aa4, the contact portion 63Aa5 may not be provided.

Figure 37:
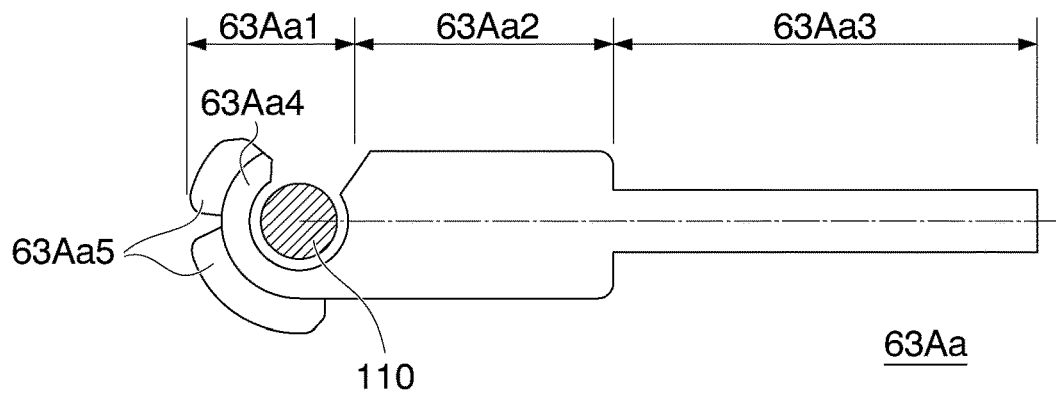
FIG. 37 is a side view showing a further modification example of the connection member in the clip device according to the fourth embodiment.

As shown in FIG. 35, the contact portion 63Aa5 is continuously formed. The contact portion 63Aa5 may be intermittently formed. In the case in which the contact portion 63Aa5 is intermittently formed, it is preferable that the contact portion 63Aa5 is formed at the region where the force received by the hook claw when pulled by the operation wire 62 is most concentrated so as to prevent the tearing in the hook claw. For example, as shown in FIG. 37, the contact portion 63Aa5 is formed at least in the region from the root of the hook claw to the distal end of the hook claw along the longitudinal direction of the connection member. For example, the plurality of contact portions that are intermittently formed may extend radially from the hook claw.

The second connection member is formed to have the contact portion that is same with the contact portion 63Aa5 of the first connection member, and the duplicate description is omitted.

The contact portion is formed in the first hook claw and the second claw to increase the contact area with the arms such that the swing between the hook claw and the arms can be prevented and the connection stability between the connection member and the arms is ensured. Particularly, the width of the hook claw where the contact portion is formed is larger than other portions of the connection member such that the rotation around the longitudinal axis of the connection member as the rotation center is effectively suppressed.

The contact portion is configured to increase the width or the thickness of the hook claw such that the strength of the hook claw is significantly increased. Accordingly, when the operation wire 62 is pulled toward the proximal end side for separating the clip and the connection member, the hook claw is separated from the first pin only due to the deformation of the hook claw such that the possibility of fracturing the hook claw is decreased.

In the case in which the contact portions are intermittently formed, the force necessary for making the hook claw to deform becomes small and the possibility of fracturing the hook claw is decreased. These forces have a trade-off relationship therebetween.

Fifth Embodiment

Compared with the fourth embodiment, the fifth embodiment is different in the structure of the two connection members. The distal end portion of the connection member according to the present embodiment it an engaging portion including two engaging claws being opposite to each other rather than the hook claws.

According to the fifth embodiment, the two connection members are the same such that the first connection member 63B will be taken as an example to describe.

Figure 38:
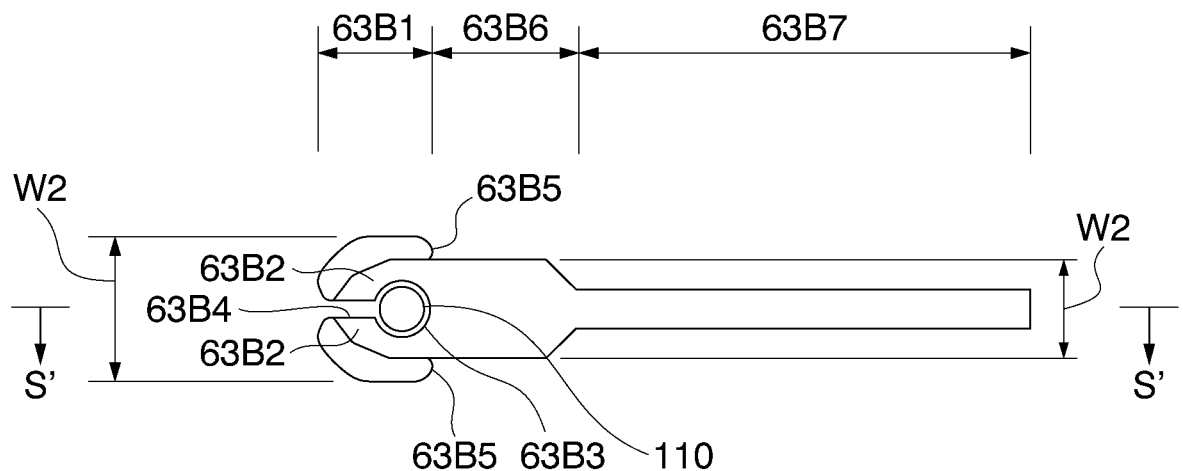
FIG. 38 is a side view showing a connection member in a clip device according to a fifth embodiment.

As shown in FIG. 38, the first connection member 63B includes an engaging portion (that is, the distal end portion) 63B1, a main body portion 63B6, and a proximal end portion 63B7.

The two engaging claws 63B2 configuring the engaging portion 63B1 form an accommodation portion 63B3 and a notch 63B4 between the two engaging claws 63B2. The accommodation portion 63B3 is configured to accommodate the first pin 110. The gap between the two engaging claws 63B2 in the notch 63B4 is smaller than the outer diameter of the first pin 110 such that it is possible to press the first pin 110 into the accommodation portion 63B3 via the notch 63B4. Accordingly, it is possible to make the first pin 110 to be fit in the space between the two engaging claws 63B2. In the state in which the first pin 110 is fit in the space between the two engaging claws 63B2, when the first pin 110 is pulled from the space between the two engaging claws 63B2, the two engaging claws 63B2 are elastically deformed and the first pin 110 is separated from the space between the two engaging claws 63B2.

The connection member 63B including the engaging portion 63B1 is a plate-shaped member, and the connection member 63B is in contact with the arms 12, 13 from the two sides so as to prevent the arms 12, 13 from moving in the axial direction of the first pin 110. When the clip 10 and the connection member 63B are separated from each other, the operation wire 62 is pulled toward the proximal end side such that the two engaging claws receive the force to be deformed and the first pin 110 is separated from the accommodation portion 63B3 via the notch 63B4, thus the connection between the connection member 63B and the first pin 110 is released.

As shown in FIG. 38, the contact portion 63B5 extends from the edge portion of the engaging claw 63B2 to increase the contact area with the arms 12, 13. The contact portion 63B5 may be integrally formed with the connection member 63B, or the contact portion 63B5 and the connection member 63B may be individually formed and then joined together. It is preferable that the width W1 of the engaging portion 63B1 where the contact portion 63B5 is formed is larger than the width W2 of the other portions of the connection member 63B.

Figure 39:
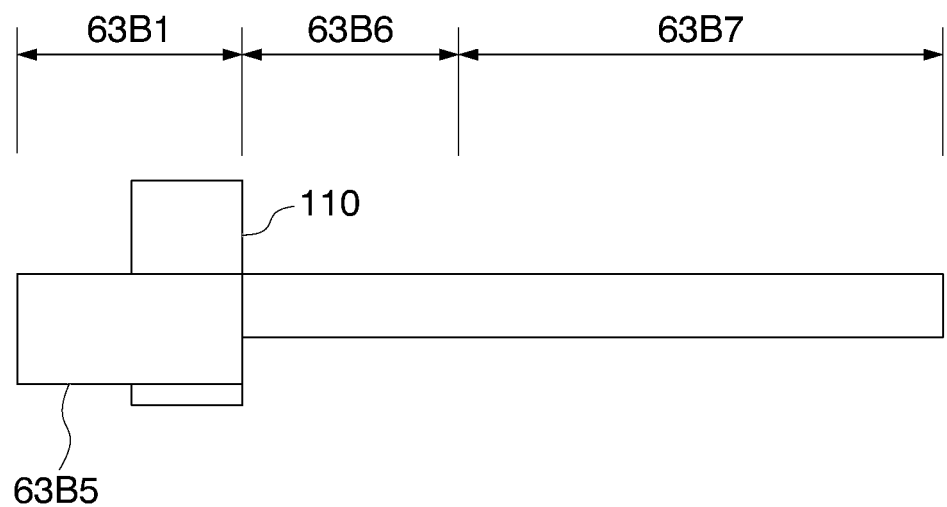
FIG. 39 is a top view showing a modification example in which the thickness of the contact portion is larger than the thickness of the engagement claw that is viewed from the direction S' shown in FIG. 38.

The thickness of the contact portion 63B5 may be the same with the thickness of the engaging claw 63B2. Otherwise, as shown in FIG. 39, the thickness of the contact portion 63B5 may be larger than the thickness of the engaging claw 63B2. In the connection member 63B, the thickness of the engaging portion 63B1 where the contact portion 63B5 is formed may be larger than the thickness of other portions of the connection member 63B. In the case in which the thickness of the engaging claw 63B2 is larger than the thickness of the main body portion 63B6 and it is possible to maintain enough strength of the engaging claw 63B2, the contact portion 63Aa5 may not be provided.

As shown in FIG. 38, the contact portion 63B5 is continuously formed. However, the contact portion 63B5 may be intermittently formed. For example, the plurality of contact portions 63B5 that are intermittently formed may extend radially from the engaging claw 63B2.

The second connection member is formed to have the contact portion that is same with the contact portion 63B5 of the first connection member, and the duplicate description is omitted.

Similar to the fourth embodiment, the contact portion is formed in the engaging portion to increase the contact area with the arms such that the swing between the hook claw and the arms can be prevented and the connection stability between the connection member and the arms is ensured. Particularly, the width of the engaging portion where the contact portion is formed is larger than other portions of the connection member such that the rotation around the longitudinal axis of the connection member as the rotation center is effectively suppressed.

The contact portion is configured to increase the width or the thickness of the engaging portion such that the strength of the engaging portion is significantly increased. Accordingly, when the operation wire 62 is pulled toward the proximal end side for separating the clip and the connection member, the engaging claw is separated from the first pin only due to the deformation of the engaging claw such that the possibility of fracturing the hook claw is decreased.

In the case in which the contact portions are intermittently formed, the force necessary for making the engaging claw to deform becomes small and the possibility of fracturing the engaging claw is further decreased. These forces have a trade-off relationship therebetween.

Although each preferred embodiment of the present invention has been described above together with each embodiment, the present invention is not limited to this embodiment and each embodiment. Configurations can be added, omitted, replaced, and other modifications without departing from the spirit of the present invention.

Further, the present invention is not limited by the above description and is limited only by the appended claims.

What is claimed is:

1. A clip device comprising:
    a clip including:
        a first arm;
        a second arm configured to open and close relative to the first arm, the second arm including:
            a first surface facing the first arm;
            a second surface located opposite the first surface;
            a first groove penetrating between the first surface and the second surface; and
            a protrusion protruding from the second surface, the protrusion located along the first groove;
    a pin inserted into the first groove;
    a pipe configured to store a proximal end portion of the clip; and
    a hook configured to hook the pin, a proximal end of the hook being configured to connect to a wire.

2. The clip device according to claim 1, wherein:
    a length of the first groove is longer than a length of the protrusion,
    the length of the first groove is a length along a longitudinal direction of the second arm, and
    the length of the protrusion is a length along the longitudinal direction of the second arm.

3. The clip device according to claim 1, wherein a proximal end of the first groove is located proximally relative to a proximal end of the protrusion.

4. The clip device according to claim 3, wherein a distal end of the first groove is located distally relative to a distal end of the protrusion.

5. The clip device according to claim 4, wherein:
    a length of the first groove is longer than a length of the protrusion,
    the length of the first groove is a length along a longitudinal direction of the second arm, and
    the length of the protrusion is a length along the longitudinal direction of the second arm.

6. The clip device according to claim 1, wherein the protrusion is spaced apart from the first groove.

7. The clip device according to claim 6, wherein the hook is in contact with the protrusion.

8. The clip device according to claim 1, wherein:
    the pin is configured to move within the first groove, and
    the second arm is configured to rotate about the pin.

9. The clip device according to claim 1, wherein a distal end of the protrusion is offset to a proximal end of the protrusion in a longitudinal direction of the second arm.

10. A clip arm including:
    a first surface;
    a second surface located opposite the first surface;
    a first groove penetrating between the first surface and the second surface; and
    a protrusion protruding from the second surface, the protrusion located along the first groove.

11. The clip arm according to claim 10, wherein:
    a length of the first groove is longer than a length of the protrusion,
    the length of the first groove is a length along a longitudinal direction of the clip arm, and
    the length of the protrusion is a length along the longitudinal direction of the clip arm.

12. The clip arm according to claim 10, wherein a proximal end of the first groove is located proximally relative to a proximal end of the protrusion.

13. The clip arm according to claim 12, wherein a distal end of the first groove is located distally relative to a distal end of the protrusion.

14. The clip arm according to claim 13, wherein:
    a length of the first groove is longer than a length of the protrusion,
    the length of the first groove is a length along a longitudinal direction of the clip arm, and
    the length of the protrusion is a length along the longitudinal direction of the clip arm.

15. The clip arm according to claim 10, wherein the protrusion is spaced apart from the first groove.

16. The clip arm according to claim 10, wherein a distal end of the protrusion is offset to a proximal end of the protrusion in a longitudinal direction of the clip arm.

17. The clip arm according to claim 16, wherein a distal end of the first groove is offset to a proximal end of the first groove in the longitudinal direction of the clip arm.

18. A clip device comprising:
    a clip including two arms;
    a pin configured to connect to the two arms such that the two arms are rotatable around the pin when connected to the pin; and
    a connection body configured to connect an operation wire and the pin, the connection body including:
        a hook located at a distal end of the connection body, the hook configured to engage with the pin; and
        a contact surface extending from the hook toward a distal end of the clip,
    wherein a thickness of the connection body is largest at the contact surface.

19. The clip device according to claim 18, wherein the hook and the contact surface are integrally unified.

20. The clip device according to claim 18, wherein the contact surface extends along a longitudinal axis of the pin.

\* \* \* \* \*